United States Patent
Perry

(10) Patent No.: US 7,809,512 B2
(45) Date of Patent: Oct. 5, 2010

(54) BIOSENSOR CODING SYSTEM

(75) Inventor: Joseph E. Perry, Osceola, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 30 days.

(21) Appl. No.: 11/938,288

(22) Filed: Nov. 11, 2007

(65) Prior Publication Data

US 2009/0125268 A1    May 14, 2009

(51) Int. Cl.
*G06F 19/00* (2006.01)
*G01N 33/487* (2006.01)

(52) U.S. Cl. .................................. 702/23; 204/403.01

(58) Field of Classification Search ................... 702/23, 702/85, 100; 204/403.01
See application file for complete search history.

(56) References Cited

U.S. PATENT DOCUMENTS

| | | | |
|---|---|---|---|
| 4,510,383 A | 4/1985 | Ruppender | |
| 4,714,874 A | 12/1987 | Morris et al. | |
| 4,929,426 A | 5/1990 | Bodai et al. | |
| 4,940,945 A | 7/1990 | Littlejohn et al. | |
| 5,281,395 A | 1/1994 | Markart et al. | |
| 5,379,214 A | 1/1995 | Arbuckle et al. | |
| 5,443,080 A | 8/1995 | D'Angelo et al. | |
| 5,445,967 A | 8/1995 | Deuter | |
| 5,462,064 A | 10/1995 | D'Angelo et al. | |
| 5,510,266 A | 4/1996 | Bonner et al. | |
| 5,575,403 A | 11/1996 | Charlton et al. | |
| 5,580,794 A | 12/1996 | Allen | |
| 5,795,543 A | 8/1998 | Poto et al. | |
| 5,830,133 A | 11/1998 | Osten et al. | |
| 5,837,546 A | 11/1998 | Allen et al. | |
| 5,856,195 A | 1/1999 | Charlton et al. | |
| 5,863,800 A | 1/1999 | Eikmeier et al. | |
| 6,377,894 B1 | 4/2002 | Deweese et al. | |
| 6,485,437 B1 | 11/2002 | Tapper | |
| 6,599,406 B1 | 7/2003 | Kawanaka et al. | |
| 6,773,671 B1 | 8/2004 | Lewis et al. | |
| 6,814,844 B2 | 11/2004 | Bhullar et al. | |

(Continued)

FOREIGN PATENT DOCUMENTS

EP    0840122    5/1998

(Continued)

OTHER PUBLICATIONS

EPO, "Search Report and Written Opinion for PCT/US2008/078534", Dec. 22, 2008, Publisher: International Searching Authority.

*Primary Examiner*—Bryan Bui
(74) *Attorney, Agent, or Firm*—Nixon Peabody LLP

(57) ABSTRACT

A biosensor system determines an analyte concentration using one or more calibrated correlation equations for an optical and/or electrochemical analysis of a biological fluid. The biosensor system may be implemented using a measurement device and a sensor strip. The measurement device applies test signals to a sequential conductive pattern on a sensor strip. The measurement device selectively and sequentially connects test contacts with conductive and non-conductive areas on the sequential conductive pattern, which generates code signals in response to the test signals. The measurement device uses the code signals to calibrate one or more of the correlation equations. The measurement device uses the calibrated correlation equations to determine the analyte concentration.

23 Claims, 10 Drawing Sheets

U.S. PATENT DOCUMENTS

| | | |
|---|---|---|
| 2001/0023324 A1 | 9/2001 | Pronovost et al. |
| 2001/0039057 A1 | 11/2001 | Douglas et al. |
| 2001/0045355 A1 | 11/2001 | Gephart et al. |
| 2002/0059030 A1 | 5/2002 | Otworth et al. |
| 2002/0082797 A1 | 6/2002 | Deweese et al. |
| 2002/0133080 A1 | 9/2002 | Apruzzese et al. |
| 2003/0013941 A1 | 1/2003 | Cohn et al. |
| 2003/0023187 A1 | 1/2003 | Tapper |
| 2003/0040682 A1 | 2/2003 | Tapper |
| 2003/0062262 A1 | 4/2003 | Mansouri et al. |
| 2003/0098233 A1 | 5/2003 | Kermani et al. |
| 2003/0109777 A1 | 6/2003 | Kloepfer et al. |
| 2003/0191415 A1 | 10/2003 | Moerman et al. |
| 2004/0012676 A1 | 1/2004 | Weiner et al. |
| 2004/0019653 A1 | 1/2004 | Debaty et al. |
| 2004/0019686 A1 | 1/2004 | Toyoda et al. |
| 2004/0106858 A1 | 6/2004 | Say et al. |
| 2004/0156832 A1 | 8/2004 | Jolly |
| 2004/0171921 A1 | 9/2004 | Say et al. |
| 2004/0200721 A1 | 10/2004 | Bhullar et al. |
| 2004/0244151 A1 | 12/2004 | Sakata et al. |
| 2004/0259180 A1 | 12/2004 | Burke et al. |
| 2005/0016845 A1 | 1/2005 | Groll et al. |
| 2005/0016846 A1 | 1/2005 | Groll et al. |
| 2005/0019805 A1 | 1/2005 | Groll |
| 2005/0019945 A1 | 1/2005 | Groll et al. |
| 2005/0019953 A1 | 1/2005 | Groll et al. |
| 2005/0023137 A1 | 2/2005 | Bhullar et al. |
| 2005/0027181 A1 | 2/2005 | Goode et al. |
| 2005/0057676 A1 | 3/2005 | Weiner et al. |
| 2005/0076845 A1 | 4/2005 | Langdale |
| 2005/0079945 A1 | 4/2005 | Wittkopp |
| 2005/0103624 A1 | 5/2005 | Bhullar et al. |
| 2005/0121322 A1 | 6/2005 | Say et al. |
| 2005/0137471 A1 | 6/2005 | Haar et al. |
| 2005/0142033 A1 | 6/2005 | Glezer et al. |
| 2005/0154271 A1 | 7/2005 | Rasdal et al. |
| 2005/0161345 A1 | 7/2005 | Groll et al. |
| 2005/0177072 A1 | 8/2005 | Kloepfer et al. |
| 2005/0179647 A1 | 8/2005 | Simmons et al. |
| 2005/0199494 A1 | 9/2005 | Say et al. |
| 2005/0226846 A1 | 10/2005 | Umlauf |
| 2005/0279647 A1 | 12/2005 | Beaty et al. |
| 2006/0042964 A1 | 3/2006 | Mansouri et al. |
| 2006/0108218 A1 | 5/2006 | Gephart et al. |
| 2006/0189895 A1 | 8/2006 | Neel et al. |
| 2009/0030617 A1 * | 1/2009 | Schell et al. .................. 702/19 |

FOREIGN PATENT DOCUMENTS

| | | |
|---|---|---|
| EP | 1152239 | 11/2001 |
| EP | 1475630 | 11/2004 |
| WO | WO 03019165 | 3/2003 |
| WO | WO 2004113914 | 12/2004 |
| WO | WO 2004113915 | 12/2004 |
| WO | WO 2005001474 | 1/2005 |
| WO | WO 2006035322 | 4/2006 |
| WO | WO 2006113723 | 10/2006 |
| WO | WO 2006113865 | 10/2006 |
| WO | WO 2007078533 | 7/2007 |
| WO | WO 2007100651 | 9/2007 |

* cited by examiner

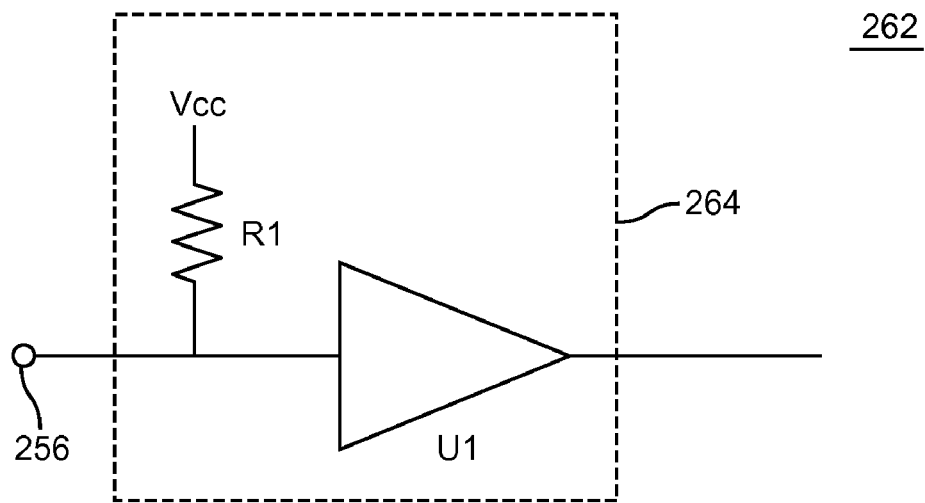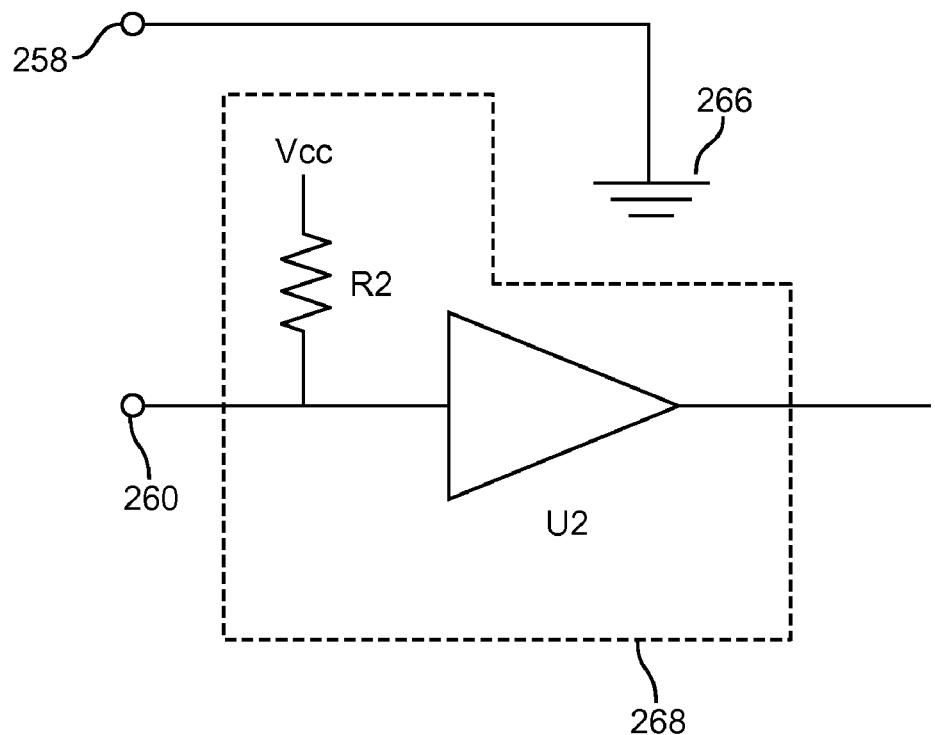
Fig.3

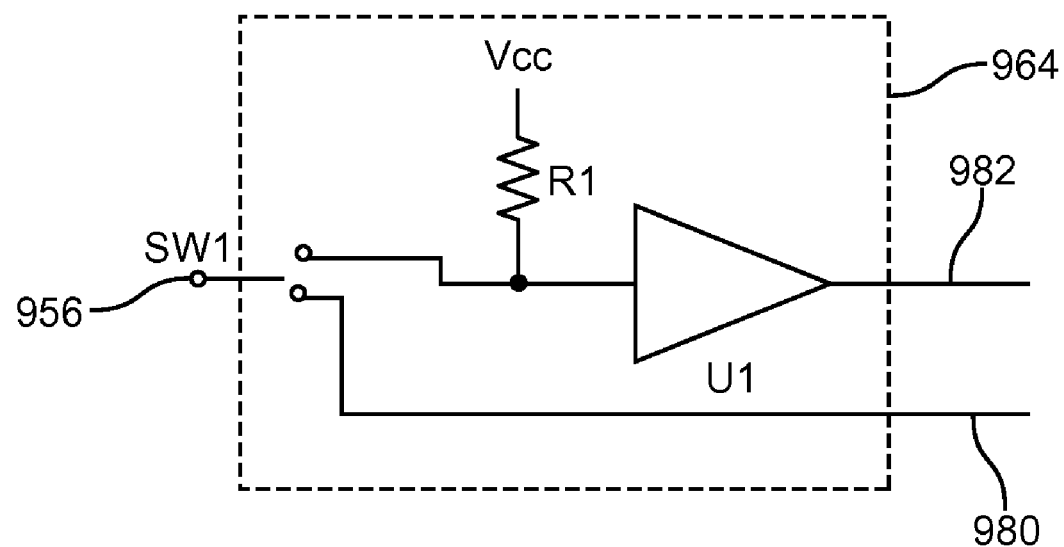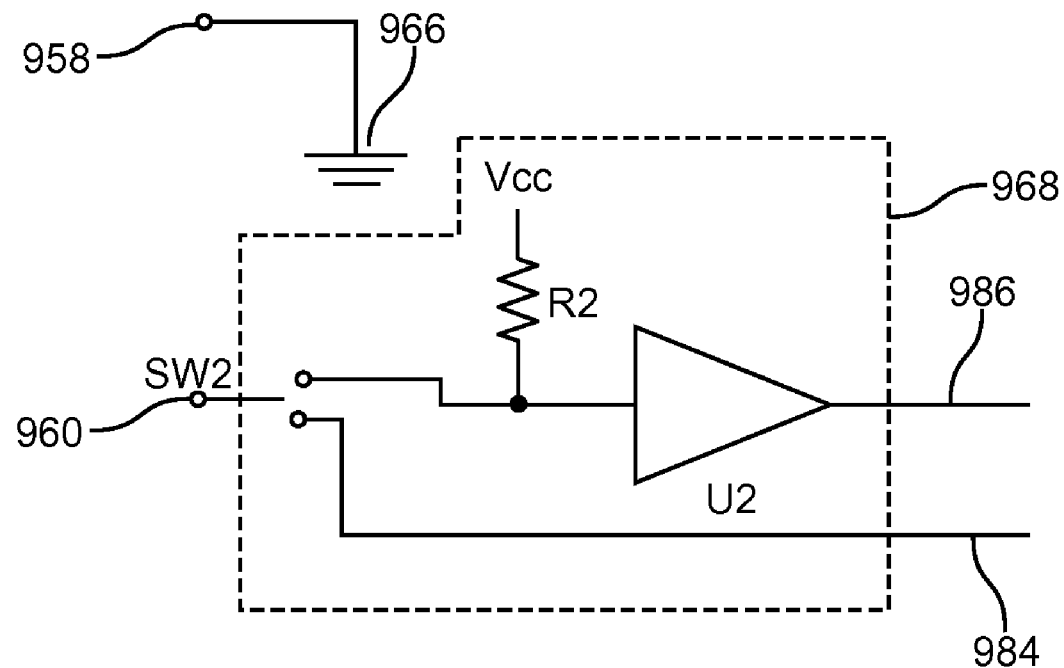
Fig. 9

BIOSENSOR CODING SYSTEM

BACKGROUND

Biosensors provide an analysis of a biological fluid, such as whole blood, urine, or saliva. Typically, biosensors have a measurement device that analyzes a sample of the biological fluid placed in a sensor strip. The analysis determines the concentration of one or more analytes, such as alcohol, glucose, uric acid, lactate, cholesterol, or bilirubin, in a sample of the biological fluid. The sample of biological fluid may be directly collected or may be a derivative of a biological fluid, such as an extract, a dilution, a filtrate, or a reconstituted precipitate. The analysis is useful in the diagnosis and treatment of physiological abnormalities. For example, a diabetic individual may use a biosensor to determine the glucose level in whole blood for adjustments to diet and/or medication.

Many biosensor systems provide calibration information to the measurement device prior to the analysis. The measurement device may use the calibration information to adjust the analysis of the biological fluid in response to one or more parameters, such as the type of biological fluid, the particular analyte(s), and the manufacturing variations of the sensor strip. The accuracy and/or precision of the analysis may be improved with the calibration information. Accuracy may be expressed in terms of bias of the sensor system's analyte reading in comparison to a reference analyte reading, with larger bias values representing less accuracy, while precision may be expressed in terms of the spread or variance among multiple measurements. If the calibration information is not read properly, the measurement device may not complete the analysis or may make a wrong analysis of the biological fluid.

Biosensors may be designed to analyze one or more analytes and may use different volumes of biological fluids. Some biosensors may analyze a single drop of whole blood, such as from 0.25-15 microliters (µL) in volume. Biosensors may be implemented using bench-top, portable, and like measurement devices. Portable measurement devices may be hand-held and allow for the identification and/or quantification of one or more analytes in a sample. Examples of portable measurement systems include the Ascensia Breeze® and Elite® meters of Bayer HealthCare in Tarrytown, N.Y., while examples of bench-top measurement systems include the Electrochemical Workstation available from CH Instruments in Austin, Tex.

Biosensors may use optical and/or electrochemical methods to analyze the sample of the biological fluid. In some optical systems, the analyte concentration is determined by measuring light that has interacted with a light-identifiable species, such as the analyte or a reaction or product formed from a chemical indicator reacting with the analyte redox reaction. In other optical systems, a chemical indicator fluoresces or emits light in response to the analyte redox reaction when illuminated by an excitation beam. In either optical system, the biosensor measures and correlates the light with the analyte concentration of the biological sample.

In electrochemical biosensors, the analyte concentration is determined from an electrical signal generated by an oxidation/reduction or redox reaction of the analyte when an input signal is applied to the sample. An enzyme or similar species may be added to the sample to enhance the redox reaction. The redox reaction generates an electrical output signal in response to the input signal. The input signal may be a current, potential, or combination thereof. The output signal may be a current (as generated by amperometry or voltammetry), a potential (as generated by potentiometry/galvanometry), or an accumulated charge (as generated by coulometry). In electrochemical methods, the biosensor measures and correlates the electrical signal with the concentration of the analyte in the biological fluid.

Electrochemical biosensors usually include a measurement device that applies an input signal through electrical contacts to electrical conductors of the sensor strip. The conductors may be made from conductive materials, such as solid metals, metal pastes, conductive carbon, conductive carbon pastes, conductive polymers, and the like. The electrical conductors typically connect to working, counter, reference, and/or other electrodes that extend into a sample reservoir. One or more electrical conductors also may extend into the sample reservoir to provide functionality not provided by the electrodes. The measurement device may have the processing capability to measure and correlate the output signal with the presence and/or concentration of one or more analytes in the biological fluid.

In many biosensors, the sensor strip may be adapted for use outside, inside, or partially inside a living organism. When used outside a living organism, a sample of the biological fluid is introduced into a sample reservoir in the sensor strip. The sensor strip may be placed in the measurement device before, after, or during the introduction of the sample for analysis. When inside or partially inside a living organism, the sensor strip may be continually immersed in the sample or the sample may be intermittently introduced to the strip. The sensor strip may include a reservoir that partially isolates a volume of the sample or be open to the sample. Similarly, the sample may continuously flow through the strip or be interrupted for analysis.

Sensor strips may include reagents that react with the analyte in the sample of biological fluid. The reagents may include an ionizing agent to facilitate the redox reaction of the analyte, as well as mediators or other substances that assist in transferring electrons between the analyte and the conductor. The ionizing agent may be an oxidoreductase, such as an analyte specific enzyme, which catalyzes the oxidation of glucose in a whole blood sample. The reagents may include a binder that holds the enzyme and mediator together.

Sensor strips may have an encoding pattern that provides coding information to the measurement device. The encoding pattern may be a separate component or may be partially or fully integrated with other components on the sensor strip. The coding information may be identification information indicating the type of sensor strip, the analyte(s) or biological fluid associated with the sensor strip, the manufacturing lot of the sensor strip, or the like. The coding information may indicate the correlation equation to use, changes to the correlation equation, or the like.

Correlation equations are mathematical representations of the relationship between the electrical signal and the analyte in an electrochemical biosensor or between light and the analyte in an optical biosensor. Correlation equations may be implemented to manipulate the electrical signal or light for determination of the analyte concentration. Correlation equations also may be implemented as a program number assignment (PNA) table of slopes and intercepts for the correlation equations, another look-up table, or the like. The measurement device uses the coding information to adjust the analysis of the biological fluid.

Many measurement devices obtain the coding information from the encoding pattern either electrically or optically. Some encoding patterns may be read only electrically or only optically. Other encoding patterns may be read electrically and optically.

Electrical encoding patterns usually have one or more electrical circuits with multiple contacts or pads. The measurement device may have one or more conductors that connect with each contact on the encoding pattern of the sensor strip. Typically, the measurement device applies an electrical signal through one or more of the conductors to one or more of the contacts on the encoding pattern. The measurement device measures the output signal from one or more of the other contacts. The measurement device may determine the coding information from the absence or presence of output signals from the contacts on the encoding pattern. The measurement device may determine the coding information from the electrical resistance of the output signals from the contacts on the encoding pattern.

In some electrical encoding patterns, the measurement device determines the coding information from the absence or presence of different contacts. The contacts may be removed, never formed, or disconnected from other parts of the electrical circuit. If the measurement device measures an output signal from the location of a contact, then the measurement device presumes a contact is present. If the measurement device does not measure an output signal, then the measurement device presumes a contact is absent.

In other electrical encoding patterns, the measurement device determines the coding information from the resistance of the electrical output signal from the contact. Typically, the amount of conductive material associated with each contact varies, thus changing the electrical resistance. Contacts may have additional or fewer layers of conductive material. The length and thickness of the connection between the contacts and the electrical circuit also may vary. The contacts may be removed, never formed, or disconnected from the electrical circuit.

Some optical encoding patterns have a sequence of lines and/or array of pads. The measurement device obtains the coding information by scanning the encoding pattern to determine the absence or presence of the lines or pads. Other optical encoding patterns have a sequence of bright and dark zones. The measurement device obtains the coding information by detecting the brightness values of the bright and dark zones.

Errors may occur with these conventional electrical and optical encoding patterns. During manufacturing, shipping, handling, and the like, the sensor strips may acquire or loose material. The additional or missing material may cause the measurement device to obtain the wrong coding information from the encoding pattern, which may prevent completion or cause a wrong analysis of the biological fluid.

In electrical encoding patterns, the additional or missing material may change or interfere with the coding information. The additional material may cover the contacts, the contact locations, or the connections between the contacts. If the additional material is conductive, the measurement device may determine that a contact is present when a contact is absent or may measure an incorrect resistance from a contact. If the additional material is non-conductive, the measurement device may determine that a contact is absent when a contact is present or may measure an incorrect resistance from a contact. Additionally, the missing material may have been part of the contacts or the connections between the contacts. Thus, the missing material may cause the measurement device to determine that a contact is absent when a contact is present or may cause the measurement device to measure an incorrect resistance.

In optical encoding patterns, the additional or missing material may change or interfere with the coding information. The additional material may cover or obstruct the encoding pattern or the gaps or spaces in the encoding pattern. The missing material may be misread as part of the encoding pattern. The additional or missing material may cause the measurement device to scan altered lines or pads.

Accordingly, there is an ongoing need for improved biosensors, especially those that may provide increasingly accurate and/or precise analyte concentration measurements. The systems, devices, and methods of the present invention overcome at least one of the disadvantages associated with encoding patterns on sensor strips used in biosensors.

SUMMARY

A biosensor system calibrates an analyte analysis to determine an analyte concentration in a biological fluid. The biosensor system applies test signals to a sequential conductive pattern of a sensor strip. The biosensor system selectively and sequentially connects test contacts with the conductive and non-conductive areas on the sequential conductive pattern, which generates two or more code signals in response to the test signals. The biosensor system uses the code signals to calibrate one or more correlation equations used to determine the analyte concentration.

A biosensor for determining an analyte concentration in a biological fluid may have a measurement device and a sensor strip. The measurement device has a processor connected to a pattern read device. The sensor strip has a sequential conductive pattern. The measurement device and sensor strip implement an analyte analysis. The analyte analysis has one or more correlation equations. The pattern read device applies test signals to the sequential conductive pattern. The sequential conductive pattern generates two or more code signals in response to the test signals. The processor calibrates one or more correlation equations in response to the code signals. The processor determines an analyte concentration responsive to one or more calibrated correlation equations.

Another biosensor for determining an analyte concentration in a biological fluid may have a measurement device and a sensor strip. The measurement device has a processor connected to a pattern read device. The pattern read device has three or more test contacts. The sensor strip has a sequential conductive pattern. The sequential conductive pattern has one or more conductive areas and one or more non-conductive areas. The pattern read device applies test signals to one or more test contacts and drives one or more test contacts to ground. The pattern read device selectively and sequentially connects the test contacts with the conductive and non-conductive areas on the sequential conductive pattern. The sequential conductive pattern generates two or more code signals in response to the test signals. The measurement device and sensor strip implement an analyte analysis. The analyte analysis has one or more correlation equations. The processor calibrates one or more correlation equations in response to the code signals. The processor determines an analyte concentration in response to one or more calibrated correlation equations.

In a method for calibrating an analysis of an analyte in a biological fluid, test signals are applied to a sequential conductive pattern. At least two code signals are generated in response to the test signals. At least one correlation equation is calibrated in response to the code signals. An analyte concentration is determined in response to at least one calibrated correlation equation.

BRIEF DESCRIPTION OF THE DRAWINGS

The invention may be better understood with reference to the following drawings and description. The components in the figures are not necessarily to scale, emphasis instead being placed upon illustrating the principles of the invention.

FIG. 3 depicts electrical detection circuitry in the pattern read device of FIG. 2.

FIG. 9 depicts another electrical detection circuit in a pattern read device.

DETAILED DESCRIPTION

A biosensor system uses coding information to analyze an analyte and to determine the analyte concentration in a sample of a biological fluid. The biosensor system has a measurement device that applies test signals to a sequential conductive pattern on a sensor strip. The sequential conductive pattern generates code signals in response to the test signals when the sensor strip is inserted into the measurement device. The code signals provide coding information, which the biosensor system may use in an optical and/or electrochemical analysis of the analyte in the biological fluid. The measurement device may use the coding information to calibrate one or more correlation equations used in the analysis of the analyte, identify the sensor strip, make a determination regarding the analyte analysis, or the like. The measurement device may determine the analyte concentration using one or more of the calibrated correlation equations.

Figure 1:
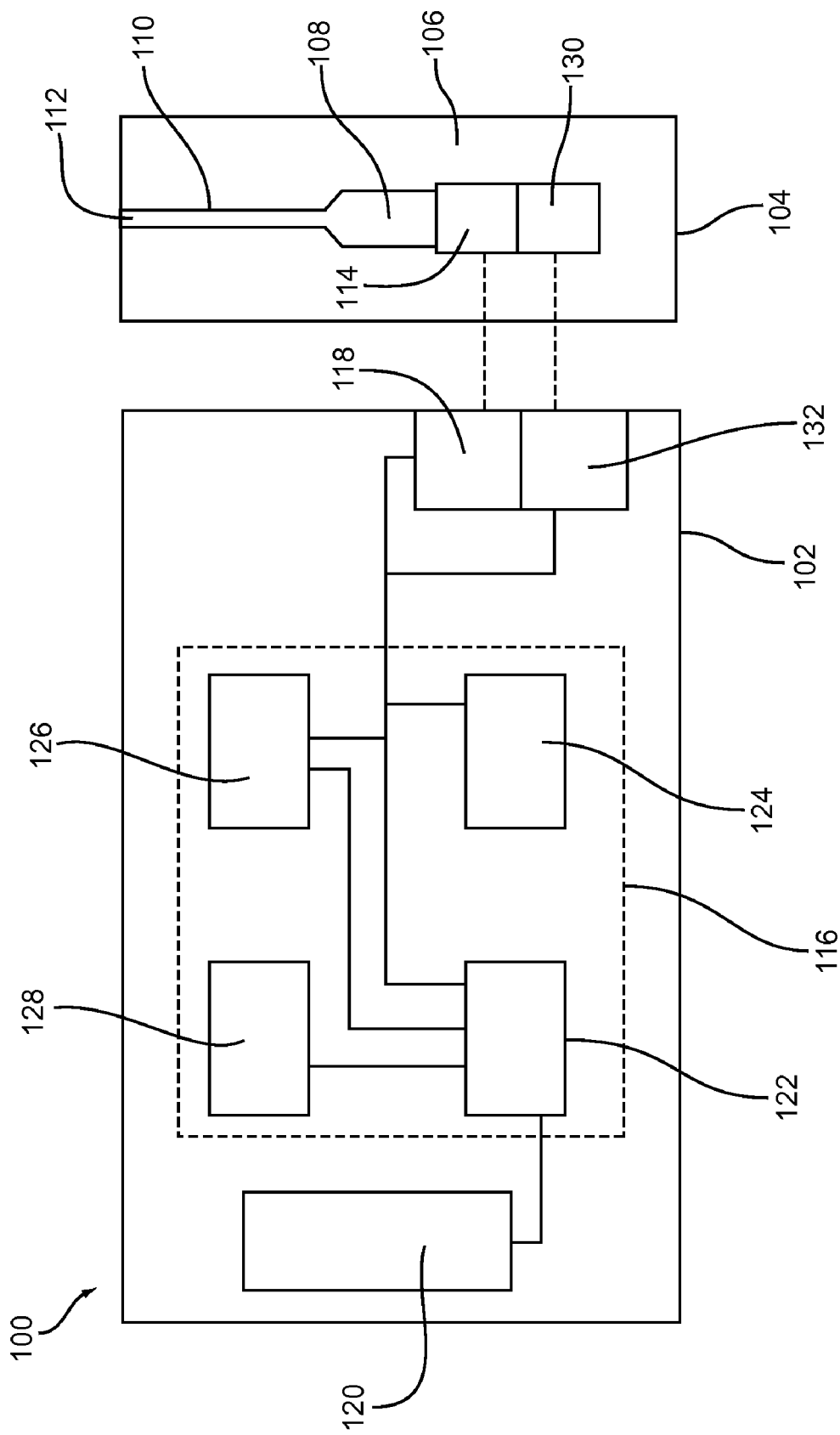
FIG. 1 depicts a schematic representation of a biosensor system that determines an analyte concentration in a sample of a biological fluid.

FIG. 1 depicts a schematic representation of a biosensor system 100 that determines an analyte concentration in a sample of a biological fluid. The biosensor system 100 includes a measurement device 102 and a sensor strip 104. The measurement device 102 may be implemented as a bench-top device, a portable or hand-held device, or the like. The measurement device 102 and the sensor strip 104 implement an analyte analysis, which may be an electrochemical analysis, an optical analysis, a combination thereof, or the like. The biosensor system 100 determines analyte concentrations, including those of alcohol, glucose, uric acid, lactate, cholesterol, bilirubin, and the like in biological samples such as whole blood and urine. While a particular configuration is shown, the biosensor system 100 may have other configurations, including those with additional components.

The sensor strip 104 has a base 106 that forms a sample reservoir 108 and a channel 110 with an opening 112. The reservoir 108 and the channel 110 may be covered by a lid with a vent. The reservoir 108 defines a partially-enclosed volume. The reservoir 108 may contain a composition that assists in retaining a liquid sample, such as water-swellable polymers or porous polymer matrices. Reagents may be deposited in the reservoir 108 and/or channel 110. The reagent composition may include one or more enzymes, binders, mediators, and the like. The reagents may include a chemical indicator for an optical system. The sensor strip 104 may have other configurations.

The sensor strip 104 may have a sample interface 114. In an electrochemical system, the sample interface 114 may have conductors connected to at least two electrodes, such as a working electrode and a counter electrode. The electrodes may be disposed on a surface of the base 106 that forms the reservoir 108. The sample interface 114 may have other electrodes and/or conductors.

The sensor strip 104 may have a sequential conductive pattern 130 on the base 106. The sequential conductive pattern 130 has intermittent conductive and non-conductive areas. "Intermittent" includes breaks in the continuity or an interrupted sequence of the conductive and non-conductive areas or the like. "Conductive" includes the capability to transmit an electrical signal and the like.

The conductive areas of the sequential conductive pattern 130 are formed by a conductive material located on the sensor strip 104. The conductive material may be the same material used to form the conductors and/or electrodes in the sample interface 114 or another component on the sensor strip 104. Conductive materials include carbon, silver, aluminum, palladium, copper, or the like. The conductive areas may be any dimension, such as a thin rectangle or trace, a wide square or rectangle, a linear or curvilinear configuration, combinations thereof, or the like. Conductive areas on the same sequential conductive pattern may have different dimensions, configurations, and/or thicknesses. The dimensions, configurations, and thickness may be selected to control or alter one or more of the code signals.

The conductive areas of the sequential conductive pattern 130 may be formed by applying conductive material onto a non-conductive material by printing or like technique. The conductive material may be disposed at selected locations on the non-conductive material with essentially the desired dimensions and thicknesses of the conductive areas. The conductive material also may be disposed as a layer on the non-conduction material with unwanted portions of the conductive material subsequently removed by laser ablation, scribing, photo etching, or like technique to form the desired dimensions of the conductive areas. The unwanted portions of the conductive layer may be removed to form one or more conductive areas of the desired dimensions and thickness at selected locations surrounded by the non-conductive areas. The unwanted portions of the conductive layer also may be removed to expose one or more non-conductive areas surrounded by the conductive areas. The conductive areas also may be formed by applying a layer of non-conductive material on a layer of electrically conductive material. Portions of the non-conductive material are subsequently removed by laser ablation, scribing, photo etching, or like technique to expose the desired dimensions of the conductive areas at selected locations. The non-conductive material forms the non-conductive areas of the sequential conductive pattern 130. The conductive and non-conductive areas may be formed using other techniques.

The sequential conductive pattern 130 may be located where the conductive and non-conductive areas are essentially aligned with one or more of the working, counter, or other electrodes on the sensor strip 104. The sequential conductive pattern 130 may be located on the top, bottom, sides, or any other location on the sensor strip 104. The sequential conductive pattern 130 may be on a separate strip. For example, the sequential conductive pattern 130 may be on a coding strip for use with a set of measuring strips. The coding strip may be another strip or may be part of or attached to a package containing the set of measuring strips. In addition, the coding strip and the measuring strips each may have a sequential conductive pattern. For example, the coding strip may have a first sequential conductive pattern that provides more general coding information. Each measuring strip may have a second sequential conductive pattern that provides more specific coding information.

The measurement device 102 includes electrical circuitry 116 connected to a sensor interface 118, a display 120, and a pattern read device 132. The sensor interface 118 and the pattern read device 132 may be the same component. The electrical circuitry 116 may include a processor 122 connected to a signal generator 124, an optional temperature sensor 126, and a storage medium 128. Electrical circuitry 116 may have other configurations including those with additional components.

The sensor strip 104 may be configured for insertion into the measurement device 102 in only one orientation. The sensor strip 104 may be configured for insertion into the measurement device with an orientation that places the sequential conductive pattern 130 in electrical communication with the pattern read device 132. The sensor strip 104 may be configured for insertion into the measurement device with an orientation that places the sample interface in electrical and/or optical communication with the sensor interface 118. "Electrical communication" includes the capability to transfer electrical or other signals wirelessly or through physical contact. "Optical communication" includes the capability to transfer light. The sensor strip 104 may have other configurations, including those with different orientations.

The processor 122 provides a control signal to the pattern read device 132. The control signal may be an electrical signal such as potential, current, or the like. The control signal operates test contacts in the pattern read device 132 that connect with the conductive and non-conductive areas in the sequential conductive pattern 130 when the sensor strip is inserted into the measurement device. The pattern read device 132 drives one test contact to ground and applies test signals to the other test contacts in response to the control signal. "Ground" includes zero or near zero potential, current, or the like.

The signal generator 124 provides an excitation signal to the sensor interface 118 in response to the processor 122. In optical systems, the excitation signal operates a light source and a detector in the sensor interface 118. In electrochemical systems, the excitation signal is transmitted by the sensor interface 118 through analysis contacts to the conductors and electrodes in the sample interface 114 to apply the excitation signal to the reservoir 108 and thus, to the sample of the biological fluid.

The excitation signal may be a potential or current and may be constant, variable, or a combination thereof, such as when an AC signal is applied with a DC signal offset. The excitation signal may be applied as a single pulse or in multiple pulses, sequences, or cycles. The signal generator 124 also may record an output signal from the sensor interface 118 as a generator-recorder.

The storage medium 128 may be a magnetic, optical, or semiconductor memory, another computer readable storage device, or the like. The storage medium 128 may be a fixed memory device or a removable memory device such as a memory card.

The processor 122 may implement analyte analysis and data treatment using computer readable software code and data stored in the storage medium 128. The processor 122 may use coding information from the sequential conductive pattern 130 to calibrate the analyte analysis and data treatment.

The processor 122 may provide the control signal to the pattern read device 132 in response to the presence of the sensor strip 104 at the sensor interface 118, user input, or the like. The processor 122 may start the analyte analysis after obtaining the coding information from the sequential conductive pattern 130. To start the analysis, the processor 122 may direct the signal generator 124 to provide the excitation signal to the sensor interface 118. The processor 122 may receive a sample temperature from the temperature sensor 126, if so equipped.

The processor 122 receives coding information from the pattern read device 132. The coding information is responsive to the conductive and non-conductive areas of the sequential conductive pattern 130. The processor 122 also receives the output signal from the sensor interface 118. The output signal is generated in response to the redox reaction of the analyte in the sample. The output signal may be generated using an optical system, an electrochemical system, or the like. The processor 122 may use a correlation equation to determine the concentration of the analyte in the sample from one or more output signals. The correlation equation may be calibrated by the processor 122 in response to the coding information from the sequential conductive pattern 130. The results of the analyte analysis are output to the display 120 and may be stored in the storage medium 128.

Correlation equations relate the analyte concentrations with the output signals and may be represented graphically, mathematically, a combination thereof, or the like. The correlation equations may be represented by a program number assignment (PNA) table, another look-up table, or the like that is stored in the storage medium 128. Instructions regarding implementation of the analysis and use of the coding information may be provided by the computer readable software code stored in the storage medium 128. The code may be object code or any other code describing or controlling the functionality described herein. The data from the analyte analysis may be subjected to one or more data treatments, including the determination of decay rates, K constants, slopes, intercepts, and/or sample temperature in the processor 122.

The sensor interface 118 is in electrical and/or optical communication with the sample interface 114. "Electrical communication" includes the transfer of excitation and output signals between the analysis contacts in the sensor interface 118 and the conductors and electrodes in the sample interface 114. "Electrical communication" may be implemented wirelessly or through physical contact. The sensor interface 118 transmits the excitation signal from signal generator 124 to the sample interface 114. The sensor interface 118 also transmits the output signal from the sample to the processor 122 and/or the signal generator 124. "Optical communication" includes the transfer of light between an optical portal in the sample interface 102 and a light source or detector in the sensor interface 108.

The pattern read device 132 is in electrical communication with the sequential conductive pattern 130. Electrical communication includes the transfer of electrical or other signals between the test contacts in the pattern read device 132 and the conductive and non-conductive areas of the sequential conductive pattern 130. Electrical communication may be implemented wirelessly or through physical contact.

The display 120 may be analog or digital. The display 120 may be a LCD, LED, or vacuum fluorescent display adapted to displaying a numerical reading.

In use, the processor 122 detects the insertion of the sensor strip into the measurement device. When the strip is inserted, the sequential conductive pattern 130 passes across the test contacts in the pattern read device 132. The processor 122 provides a control signal to the pattern read device 132, which drives one test contact to ground and applies test signals to other test contacts. As the pattern read device 132 passes across the sequential conductive pattern 130, the test contacts selectively and sequentially connect with the intermittent conductive and non-conductive areas. The conductive areas connect the non-ground test contacts with the test contact driven to ground. The non-conductive areas essentially prevent electrical communication between the test contacts. The switching between ground test signals and non-ground test signals generates the code signals. The pattern read device 132 receives code signals from the sequential conductive pattern 130 in response to the test signals. The pattern read device 132 provides the code signals to the processor 122.

After the sensor strip is inserted into the measurement device, a liquid sample for analysis is transferred into the reservoir 108 by introducing the liquid to the opening 112. The liquid sample flows through the channel 110 and into the reservoir 108, while expelling the previously contained air. The liquid sample chemically reacts with the reagents deposited in the channel 110 and/or the reservoir 108.

The processor 122 directs the signal generator 124 to provide the excitation signal to the sensor interface 118. In optical systems, the sensor interface 118 operates the detector and light source in response to the excitation signal. In electrochemical systems, the sensor interface 118 provides the excitation signal to the sample through the sample interface 114. The processor 122 receives an output signal generated in response to the redox reaction of the analyte in the sample. The processor 122 determines the analyte concentration of the sample using one or more correlation equations. The processor 122 may calibrate the correlation equations in response to the coding information from the sequential conductive pattern 130. The determined analyte concentration may be displayed and/or stored for future reference.

The measurement device 102 and the sensor strip 104 may implement an electrochemical analysis, an optical analysis, a combination thereof, or the like to determine one or more analyte concentrations in a sample of biological fluid. Optical analyses use the reaction of a chemical indicator with an analyte to determine the analyte concentration in the biological fluid. Electrochemical analyses use an oxidation/reduction or redox reaction of an analyte to determine the analyte concentration in the biological fluid.

An optical analysis generally measures the amount of light absorbed or generated by the reaction of a chemical indicator with the analyte. An enzyme may be included with the chemical indicator to enhance the reaction kinetics. The light from an optical system may be converted into an electrical signal, such as current or potential.

In light-absorption optical analyses, the chemical indicator produces a reaction product that absorbs light. An incident excitation beam from a light source is directed toward the sample. The incident beam may be reflected back from or transmitted through the sample to a detector. The detector collects and measures the attenuated incident beam. The amount of light attenuated by the reaction product is an indication of the analyte concentration in the sample.

In light-generated optical analyses, the chemical detector fluoresces or emits light in response to the analyte during the redox reaction. A detector collects and measures the generated light. The amount of light produced by the chemical indicator is an indication of the analyte concentration in the sample.

During electrochemical analyses, an excitation signal is applied to the sample of the biological fluid. The excitation signal may be a potential or current and may be constant, variable, or a combination thereof. The excitation signal may be applied as a single pulse or in multiple pulses, sequences, or cycles. The analyte undergoes a redox reaction when the excitation signal is applied to the sample. An enzyme or similar species may be used to enhance the redox reaction of the analyte. A mediator may be used to maintain the oxidation state of the enzyme. The redox reaction generates an output signal that may be measured constantly or periodically during transient and/or steady-state output. Steady-state is when the change of a signal with respect to its independent input variable (time, etc.) is substantially constant, such as within ±10 or ±5%. Various electrochemical processes may be used such as amperometry, coulometry, voltammetry, gated amperometry, gated voltammetry, and the like.

The optical and electrochemical analyses use correlation equations to determine the analyte concentration of the biological fluid in the sample. Correlation equations are mathematical representations of the relationship between analyte concentrations and output signals such as light, current, or potential. The correlation equations may be linear, near linear, or curvilinear and may be described by a second order polynomial. From a correlation equation, an analyte concentration may be calculated for a particular output signal.

A biosensor may have one or more correlation equations stored in a memory for use during the optical or electrochemical analysis. Different correlation equations may be needed, especially when different sensor strips are used or operating parameters such as the sample temperature change. Correlation equations may be implemented to manipulate the output signal for determination of the analyte concentration. Correlation equations also may be implemented as a program number assignment (PNA) table of the slope and intercept for the correlation equations, another look-up table, or the like for comparison with the output signals to determine the analyte concentration.

In FIG. 1, the measurement device 124 may calibrate the correlation equations in response to the coding information from the sensor strip 104. The measurement device 124 may use the coding information to identify the type or other feature of the sensor strip, to determine whether to analyze the sample in the sensor strip, or the like.

The pattern read device 132 provides the code signals from the sequential conductive pattern 130 to the processor 122. The pattern read device 132 and/or processor 122 may combine the code signals to form a check signal. "Combine" includes summing, comparing, and the like operations on the code signals. The check signal may be used to identify errors, adjust the code signals for variability in the insertion rate of the sensor strip into the measurement device, or the like. The code and check signals may be digital signals or the like. "Digital signals" includes electrical signals that discretely switch between the presence and absence of current, switch between high and low potentials, or the like. "Discretely switch" includes substantially instantaneous transitions from one current, potential, or signal level to another. Digital signals may be transmitted as binary or other code. The processor 122 converts the code signals into the coding information for use with the sensor strip 104. In response to the code and check signals, the processor 122 may calibrate one or more of the correlation equations, identify the sensor strip, make a determination regarding the analyte analysis, a combination thereof, or the like.

The coding information may be any information used to calibrate one or more correlation equations, identify the sensor strip or features of the sensor strip such as the reagent or the like, make a determination regarding the analysis, a combination thereof, or the like. "Calibrate" may include adjusting or modifying the concentration value or other result of a correlation equation. "Calibrate" may include selecting one or more correlation equations. The coding information may be identification information indicating the type of sensor strip, analyte(s) or biological fluid associated with the sensor strip, the manufacturing lot of the sensor strip, the expiration date of the sensor strip, or the like. The processor 122 may select one or more correlation equations to use in response to the identification information. "Calibrate" may include modifying one or more correlation equations. The coding information may provide or direct the use of an addition or subtraction to the slope and/or intercept of a correlation equation. "Calibrate" may include providing one or more of the correlation equations. The coding information may include or direct the use of a slope and intercept for a correlation equation. Other coding information may be used.

To obtain coding information, the pattern read device 132 receives the code signals generated by the intermittent conductive and non-conductive areas on the sequential conductive pattern 130. When the sensor strip 104 is inserted into the measurement device 102, the pattern read device 132 drives one test contact to ground and applies test signals to the other test contacts. The test contacts in the pattern read device 132 pass across the sequential conductive pattern 130 to generate the code signals. The number of code signals is responsive to the arrangement of conductive and non-conductive areas in the sequential conductive pattern 130 and the number of test contacts in the pattern read device 132.

The test contacts selectively and sequentially connect with the conductive and nonconductive areas at different positions; which generates one or more code signals. "Selectively connects" may include having conductive areas at selected positions on a sequential read pattern, where one or more conductive areas connect only one selected non-ground test contact with the test contact driven to ground. "Selectively connects" may include having conductive areas at selected positions on a sequential read pattern, where one or more conductive areas connect all but one of selected non-ground test contacts with the test contact driven to ground. "Selectively connects" may include having conductive areas at selected positions on the sequential read pattern, where one or more selected conductive areas connect all non-ground test contacts with the test contact driven to ground. "Selectively connects" may include having one or more non-conductive areas aligned with the conductive areas at selected positions on a sequential read pattern, where one or more non-conductive areas connect with one or more selected non-ground test contacts when a conductive area connects the other non-ground test contacts with the test contact driven to ground. "Sequentially connects" may include moving a sequential conductive pattern in a selected direction across a pattern read device, where the conductive area and any aligned non-conductive areas connect with the test contacts in a selected order. The selected conductive areas, connections, positions, contacts, direction, order, and the like may be chosen during manufacture of the sensor strip and/or measurement device.

At a particular position, the conductive area connects the ground test contact with one or more non-ground test contacts. The ground test contact drives the non-ground test contacts to ground. Thus, the test signals of the test contacts connected with the conductive area are driven to ground at this position. In contrast, the non-conductive area connects with one or more non-ground test contacts. The non-conductive area essentially prevents electrical communication with these non-ground test contacts. Thus, the test signals of the test contacts connected with the non-conductive area remain substantially the same.

At different positions on the sequential read pattern 130, the conductive and non-conductive areas may connect with the same or different non-ground test contacts as the other position. When the connections with the conductive and non-conductive areas are the same, the ground and non-ground test contacts at this position are essentially the same as the ground and non-ground test contacts at the other position. The same ground and non-ground test contacts produce the same ground and non-ground test signals. When the connections with the conductive and non-conductive areas are different, the ground and non-ground test contacts at this position are different than the ground and non-ground test contacts at the other position. The different ground and non-ground test contacts produce different ground and non-ground test signals at each position.

As the sequential conductive pattern 130 moves across the pattern read device 132, test contacts selectively connect with conductive and nonconductive areas at each position in sequence. When connections are the same, the ground and non-ground test signals are essentially the same. When connections are different, the ground and non-ground test signals are different. This selective and sequential switching or non-switching between ground and non-ground test signals generates the code signals.

While an implementation is described using ground and non-ground test signals, the code signals may be generated using a test contact driven to a different potential, current, or signal level than the test signals applied to the other test contacts. The switching between the different potentials, currents, or signal levels would generate the code signals.

The code signals are essentially digital signals that represent the switching between ground and non-ground test signals as the test contacts in the pattern read device 132 selectively and sequentially connect with the intermittent conductive and non-conductive areas in the sequential conductive pattern 130. While the switching between ground and non-ground test signals is substantially discrete, there may be a contact bounce when the test contacts engage and disengage the conductive and/or non-conductive areas. When the contact bounce occurs, the signal may have a very rapid switching burst where the signal oscillates quickly between ground and non-ground for a short duration.

Figure 2:
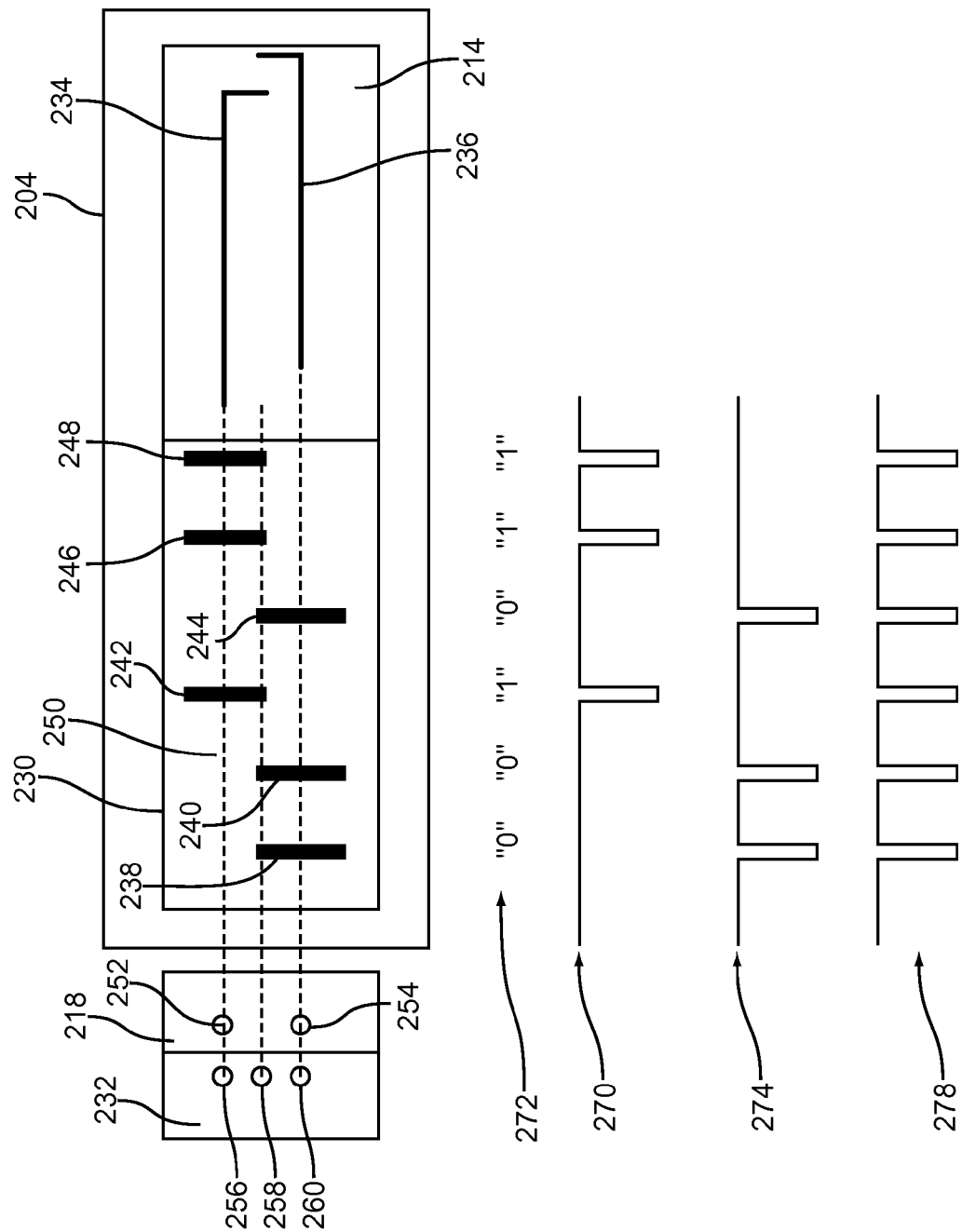
FIG. 2 depicts a sensor strip adjacent to a sensor interface and a pattern read device along with the code and check signals generated by the sensor strip.

FIG. 2 depicts a sensor strip 204 adjacent to a sensor interface 218 and a pattern read device 232 along with code and check signals generated by the sensor strip 204. While a particular configuration is shown, the sensor strip 204, the sensor interface 218, and the pattern read device 232 may have other configurations including those with additional components. Other code signals may be generated.

The sensor strip 204 includes a sample interface 214 and a sequential conductive pattern 230. The reservoir, channel, and opening of the sensor strip have been omitted for clarity. The sample interface 214 includes a working electrode 234 and a counter electrode 236. The sequential conductive pattern 230 has conductive areas 238, 240, 242, 244, 246, and 248 disposed on a non-conductive layer, which forms nonconductive areas 250. The conductive areas 238, 240, 242, 244, 246, and 248 may be traces or thin rectangles of conductive material disposed sequentially in positions essentially equidistant from each other in the sequential conductive pattern. The conductive areas 238, 240, 242, 244, 246, and 248 are disposed substantially perpendicular to the direction the sensor strip 204 moves when inserted into a measurement device. The conductive areas 238, 240, 242, 244, 246, and 248 may have other configurations and may be disposed in different positions and/or orientations.

The sensor interface 218 includes a first analysis contact 252 and a second analysis contact 254. When the sensor strip 204 is inserted properly into a measurement device, the first analysis contact 252 and the second analysis contact 254 connect with the working electrode 234 and the counter electrode 236, respectively, in the sample interface 214. A processor in the measurement device applies an excitation signal to the working and counter electrodes 234 and 236 through the first and second analysis contacts 252 and 254. The processor does not attempt to apply the excitation signal until the working and counter electrodes 234 and 236 pass the sequential conductive pattern 230.

The pattern read device 232 includes a first test contact 256, a second test contact 258, and a third test contact 260. When the sensor strip is inserted into the measurement device, the processor in the measurement device drives test contact 258 to ground and applies test signals to test contacts 256 and 258. As the sensor strip 204 passes across the pattern read device 232, the test contacts 256, 258, and 260 selectively and sequentially connect with conductive areas 238, 240, 242, 244, 246, and 248 and non-conductive area 250 in the sequential conductive pattern 230. When the test contacts 256 and 258 connect with the conductive areas 242, 246, and 248, the test contact 260 connects with the non-conductive areas 250 in the sequential conductive pattern 230. When the test contacts 258 and 260 connect with the conductive areas 238, 240, and 244, the test contact 256 connects with the non-conductive areas 250 in the sequential conductive pattern 230. The conductive areas 238, 240, 242, 244, 246, and 248 have a length selected to connect the second test contact 258 with either the first test contact 256 or the third test contact 260, but not the other test contact. One or more of the conductive areas 238, 240, 242, 244, 246, and 248 may have a length selected to connect the second test contact 258 with both the first test contact 256 and the third test contact 260.

FIG. 3 depicts electrical detection circuitry 262 in the pattern read device 232 of FIG. 2. The electrical detection circuitry 262 includes a first buffer circuit 264 connected to the first test contact 256, a ground 266 connected to the second test contact 258, and a second buffer circuit 268 connected to the third test contact 260 of FIG. 2. The first buffer circuit 264 includes input potential $V_{cc}$ connected through resister R1 to the first test contact 256 and the input of a buffer U1. The second buffer circuit 268 includes input potential $V_{cc}$ connected through resister R2 to the third test contact 260 and the input of a buffer U2. Other electrical detection circuitry may be used.

Referring to FIG. 2, when the first test contact 256 connects with the second test contact 258 through a conductive area on the sequential conductive pattern 230, the input of buffer U1 becomes ground and the corresponding output of buffer U1 is at logic zero ("0"). When the first test contact 256 connects with a non-conductive area on the sequential conductive pattern 230, the input of buffer U1 is pulled high by the input resistor R1 and the corresponding output of buffer U1 is at logic one ("1"). The sequential output of the buffer U1 generates a first code signal.

When the third test contact 260 connects with the second test contact 258 through a conductive area on the sequential conductive pattern 230, the input of buffer U2 becomes ground and the corresponding output of buffer U2 is at logic zero ("0"). When the third test contact 260 connects with a non-conductive area on the sequential conductive pattern 230, the input of buffer U2 is pulled high by the input resistor R1 and the corresponding output of buffer U2 is at logic one ("1"). The sequential output of the buffer U2 generates a second code signal.

The outputs of buffers U1 and U2 may be designated by "0" and "1" patterns depending upon whether the buffer inputs are ground or not, respectively. The "0" and "1" patterns shown in FIG. 2 were selected arbitrarily to identify the buffer output associated with a particular input. The patterns may be interchanged. Other patterns may be used and may result in different digital representations.

FIG. 2 also depicts the first and second code signals 270 and 274 generated by the sensor strip 204. The first code signal 270 illustrates the sequential connections of the first test contact 256 with the non-conductive areas 250 and the conductive areas 242, 246, and, 248 in the sequential conductive pattern 230. When the first test contact 256 connects with the conductive areas 242, 246, and, 248, the first test contact 256 connects with the second test contact 258 and thus is grounded. The second code signal 274 illustrates the sequential connections of the third test contact 260 with the non-conductive areas 250 and the conductive areas 238, 240, and, 244 in the sequential conductive pattern 230. When the third test contact 260 connects with the conductive areas 238, 240, and, 244, the third test contact 260 connects with the second test contact 258 and thus is grounded. The first code signal 270 and second code signal 274 may be represented by a logic sequence 272, in which a logic value (0 or 1) indicates the relative output of the code signals at positions on the sensor strip 204. For example, the logic value "0" indicates the first code signal 270 is not grounded and the second code signal 274 is grounded. The logic value "1" indicates the first code signal 270 is grounded and the second code signal 274 is not grounded. Other code signals, logic values, and logic sequences may be used.

The first and second code signals 270 and 274 and/or the logic sequence 272 may be used to provide coding information to a measurement device in a biosensor system. The measurement device may use the code signals and/or logic sequence to calibrate one or more correlation equations for the analyte analysis, identify the sensor strip or features of the sensor strip, make a determination regarding the analysis, a combination thereof, or the like. The measurement device may adjust or modify the concentration value or other result of a correlation equation, select one or more correlation equations, or the like in response to the code signals and/or logic sequence. The measurement device may use the code signals and/or logic sequence to identify the type of sensor strip, analyte(s) or biological fluid associated with the sensor strip, the manufacturing lot of the sensor strip, the expiration date of the sensor strip, or the like. The measurement device may select one or more correlation equations to use or may modify one or more correlation equations in response to the identification information. The code signals and/or logic sequence may provide or direct the use of an addition or subtraction to the slope and/or intercept of a correlation equation. The code signals and/or logic sequence may provide one or more of the correlation equations and may include or direct the use of a slope and intercept for a correlation equation. The code signals and/or logic sequence may provide other coding information.

The code signals represent the sequential connections between the test contacts and conductive and non-conductive areas in the sequential conductive pattern. The first code signal 270 represents the sequential connections between the first test contact 256 and the conductive and non-conductive areas in the sequential conductive pattern 230. Similarly, the second code signal 274 represents the sequential connections between the third test contact 260 and the conductive and non-conductive areas in the sequential conductive pattern 230. The sequential connections between the test contacts and the conductive and non-conductive areas generate unique code signals that provide coding information to the measurement device.

Different coding information may be generated by changing the location of the conductive areas in the sequential conductive pattern 230. For example, when one or more of the conductive areas 238, 240, and 244 are moved to connect the second test contact 258 with the first test contact 256; then third test contact 260 becomes connected with the non-conductive areas 250. The first and second code signals 270 and 274 would change. In the first code signal 270, one or more of the previously non-ground outputs would change to a ground output in response to the moved conductive areas 238, 240, and 244. In the second code signal 274, one or more of the previously ground outputs would change to a non-ground output in response to the moved conductive areas 238, 240, and 244.

Similarly, when one or more of the conductive areas 242, 246, and 248 are moved to connect the second test contact 258 with the third test contact 260; then first test contact 256 would be connected to the non-conductive areas 250. Thus, the first and second code signals 270 and 274 would change. In the first code signal 270, one or more of the previously ground outputs would change to a non-ground output in response to the moved conductive areas 242, 246, and 248. In the second code signal 274, one or more of the previously non-ground outputs would change to a ground output in response to the moved conductive areas 242, 246, and 248. Other changes to the connections between the tests contacts and the conductive and non-conductive areas may be made.

The number of different code sequences depends upon the number of conductive areas in the sequential conductive pattern used to generate the two code signals. For example, the sequential conductive pattern 230 uses six conductive areas to generate the first and second code signals 270 and 274. The arrangement of the conductive areas may be changed to generate up to 64 different code sequences for providing coding information to the measurement device.

Table 1 lists the number of different code sequences that binary coding (base 2) in relation to the number of conductive areas in a sequential read pattern. Other numbers of conductive areas may be used.

TABLE 1

| Number of Conductive Areas | Number of Different Code Sequences |
| --- | --- |
| 1 | 2 |
| 2 | 4 |
| 3 | 8 |
| 4 | 16 |
| 5 | 32 |
| 6 | 64 |
| 7 | 128 |
| 8 | 256 |
| 9 | 512 |
| 10 | 1024 |

Two or more code signals may be used to detect fault conditions that affect or change the coding information. Errors with the coding information may occur when a fault condition happens. A fault condition exists when two test contacts are connected when the two test contacts should not be connected. A fault condition also exists when two test contacts are not connected when the two test contacts should be connected. Other fault conditions may occur. A fault condition may be due to unexpected connections and open circuit conditions from debris on the test contact, additional material or debris on the sensor strip, missing material or a scratch in the sequential conductive pattern on the sensor strip, a combination thereof, and the like.

When two code signals are generated by the sequential read pattern, a measurement device may use encoding rules to detect fault conditions. The encoding rules include: (1) when a position of the first control signal is ground, the corresponding position of the second control signal is non-ground; (2) when a position of the first control signal is non-ground, the corresponding position of the second control signal is ground; (3) when a position of the second control signal is ground, the corresponding position of the first control signal is non-ground; and (4) when a position of the second control signal is non-ground, the corresponding position of the first control signal is ground. The encoding rules may be adapted similarly for use with three or more code signals. Other encoding rules may be used.

To detect fault conditions, the measurement device compares buffer outputs at one or more corresponding positions of the first and second control signals. The measurement device detects a fault condition when the first and second code signals have essentially the same buffer output at one or more corresponding positions. For example, the measurement device may detect a fault condition when the buffer output is a logic zero at the same position in both the first and second code signals. A logic zero buffer output indicates the buffer input is ground for both the first and second code signals at that position. The ground buffer input indicates the ground test contact is connected to both non-ground test contacts. Similarly, the measurement device may detect a fault condition when the buffer output is a logic one at the same position in both the first and second code signals. A logic one buffer output indicates the buffer input is non-ground for both the first and second code signals at that position. The non-ground buffer input indicates the ground test contact is not connected to either non-ground test contact. The measurement device may detect other fault conditions. When a fault condition is detected, the measurement device may reject the sensor strip and/or may generate an error signal.

The multiple signals produced by inserting a sensor strip into a measuring device allows for inherent error checking of the coding information. The error checking may be obtained by enforcing rules regarding the signals that are simultaneously electrically generated as the sensor strip is inserted into the measuring device. For example, if the rule is only N of the M signals can be simultaneously electrically connected, and then faulty patterns or readings may not be erroneously interpreted as a valid calibration code. The measuring device thus may detect faulty patterns or readings and reject a sensor strip before an erroneous test result is reported or after the error is detected.

These encoding rules are in response to each conductive area on the sequential read pattern connecting the ground test contact with only one of the non-ground test contacts. However, the ground test contact may connect with both of the non-ground test contacts at one or more positions on the sequential read pattern. The connection of the ground test contact with both non-ground test contacts, preferably at the first position to reach the pattern read device may enable the measurement device to identify the sensor strip, calibrate the analyte analysis, or the like more quickly.

FIG. 2 further depicts a check signal 278 generated by the sensor strip 204. The check signal 278 may be represented by a logic sequence. The measurement device combines the first and second code signals 270 and 274 to produce the check signal 278. Other check signals may be used.

The measurement device may use the check signal 278 to detect fault conditions in the first and second code signals. When a fault condition occurs, both buffer outputs may be a logic zero or a logic one at the same position in the first and second code signals. When these first and second code signals with a fault condition are compared, the output at the position of the fault condition may be indicated in the logic sequence.

The check signal 278 makes the code signals less sensitive or insensitive to the speed or changes in the speed in which the sensor strip is inserted into the measurement device. The check signal 278 provides the measurement device with a "self-clocking" capability. The check signal 278 enables the measurement device to determine when transitions of the buffer outputs occur in the first and second code signals. Buffer transitions occur when the buffer input changes from non-ground to ground or from ground to non-ground (from "1" to "0" or from "0" to "1"). Thus, the measurement device can determine when the next bit of the code signal, or transition from the buffer output, is available in each of the first and second code signals.

Figure 4:
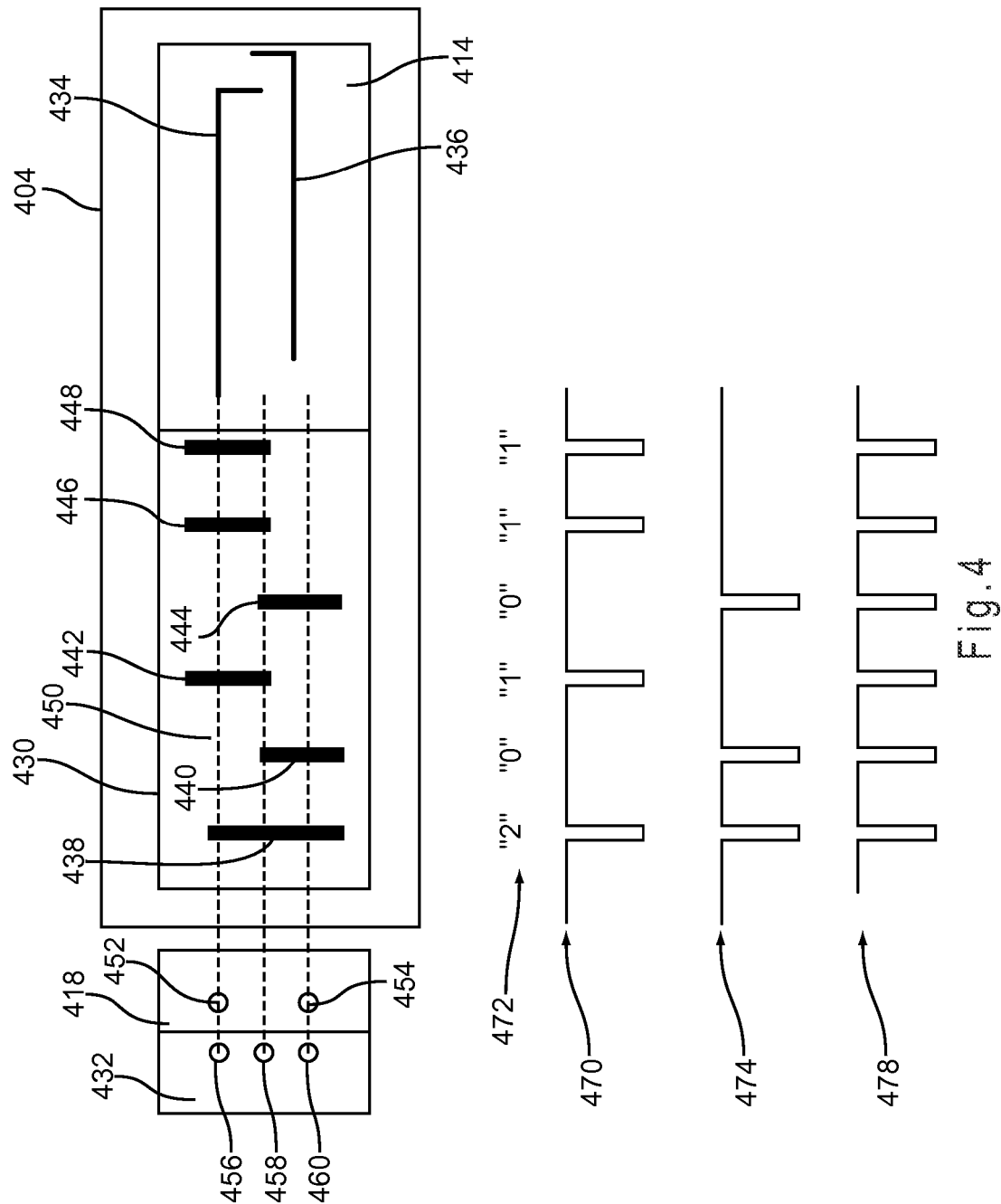
FIG. 4 depicts another sensor strip adjacent to a sensor interface and a pattern read device along with code and check signals generated by the sensor strip.

FIG. 4 depicts another sensor strip 404 adjacent to a sensor interface 418 and a pattern read device 432 along with code and check signals generated by the sensor strip 404. Sensor strip 404 is similar in configuration and operation to the sensor strip 204 described in relation to FIG. 2. Except in sensor strip 404, a conductive area 438 is used to connect the ground test contact with all the non-ground test contacts in pattern read device 438. While a particular configuration is shown, the sensor strip 404, the sensor interface 418, and the pattern read device 432 may have other configurations including those with additional components. Other code signals may be generated.

The sensor strip 404 includes a sample interface 414 and a sequential conductive pattern 430. The reservoir, channel, and opening of the sensor strip have been omitted for clarity. The sample interface 414 includes a working electrode 434 and a counter electrode 436. The sequential conductive pattern 430 has conductive areas 438, 440, 442, 444, 446, and 448 disposed on a non-conductive layer, which forms non-conductive areas 450. The conductive areas 438, 440, 442, 444, 446, and 448 may have other configurations and may be disposed in different positions and orientations.

The sensor interface 418 includes a first analysis contact 452 and a second analysis contact 454. When the sensor strip 404 is inserted properly into a measurement device, the first analysis contact 452 and second analysis contact 454 connect with the working electrode 434 and the counter electrode, respectively, in the sample interface 414.

The pattern read device 432 includes a first test contact 456, a second test contact 458, and a third test contact 460. When the sensor strip is inserted into the measurement device, the processor in the measurement device drives test contact 458 to ground and applies test signals to test contacts 456 and 458. As the sensor strip 404 passes across the pattern read device 432, the test contacts 456, 458, and 460 selectively and sequentially connect with conductive areas 438, 440, 442, 444, 446, and 448 and the non-conductive areas 450 in the sequential conductive pattern 430. When test contacts 456, 458, and 460 connect with conductive area 438, there are no test contacts connected to the non-conductive areas 450. When test contacts 456 and 458 connect with the conductive areas 442, 446, and 448, the test contact 460 connects with the non-conductive areas 450. When the test contacts 458 and 460 connect with the conductive areas 440, and 444, the test contact 456 connects with the non-conductive areas 450.

The conductive areas 440, 442, 444, 446, and 448 have a length selected to connect the second test contact 458 with either the first test contact 456 or the third test contact 460, but not the other test contact. The conductive area 438 has a length selected to connect the second test contact 458 with both the first test contact 456 and the third test contact 460. Alternatively or additionally, one or more of the other conductive areas 440, 442, 444, 446, and 448 may have a length selected to connect the second test contact with both the first test contact 456 and the third test contact 460. The connection of the second test contact 458 with the first test contact 456 and the second test contact 460 may enable the measurement device to identify the sensor strip, calibrate the analyte analysis, or the like more quickly.

FIG. 4 also depicts the first and second code signals 470 and 474 generated by the sensor strip 404. The first code signal 470 illustrates the sequential connections of the first test contact 456 with the non-conductive areas 450 and the conductive areas 438, 442, 446, and, 448 in the sequential conductive pattern 430. When the first test contact 456 connects with the conductive areas 438, 442, 446, and, 448, the first test contact 456 connects with the second test contact 458 and thus is grounded. The second code signal 474 illustrates the sequential connections of the third test contact 460 with the non-conductive areas 450 and the conductive areas 438, 440, and, 444 in the sequential conductive pattern 430. When the third test contact 460 connects with the conductive areas 438, 440, and, 444, the first test contact 460 connects with the second test contact 458 and thus is grounded. The first code signal 470 and second code signal 474 may be represented by a logic sequence 472, in which a logic value (0, 1, or 2) indicates the relative output of the code signals at positions on the sensor strip 404. For example, the logic value "0" indicates the first code signal 470 is not grounded and the second code signal 474 is grounded. The logic value "1" indicates the first code signal 470 is grounded and the second code signal 474 is not grounded. The logic value "2" indicates both the first code signal 470 and the second code signal 474 are grounded. Other code signals, logic values, and logic sequences may be used.

The first and second code signals 470 and 474 and/or logic sequence 472 may be used to provide coding information to a measurement device in a biosensor system as previously discussed. The code signals represent the sequential connections between the test contacts and conductive and non-conductive areas in the sequential conductive pattern. The sequential connections between the test contacts and the conductive and non-conductive areas generate unique code signals that provide coding information to the measurement device. Different coding information may be generated by changing the location of the conductive areas in the sequential conductive pattern 430. The first and second code signals 470 and 474 also may be used to detect fault conditions that affect or change the coding information as previously discussed.

FIG. 4 further depicts a check signal 478 generated by the sensor strip 404. The check signal 478 may be represented by a logic sequence. The check signal 478 indicates the position of the other outputs. The measurement device combines the first and second code signals 470 and 474 to produce the check signal 478. Other check signals may be used. The measurement device may use the check signal 478 to detect fault conditions in the first and second code signals as previously discussed, except that the connection of test contacts 456, 458, and 460 with conductive area 438 at the first output or position would not indicate a fault condition. The check signal 478 also makes the code signals less sensitive or insensitive to the speed or changes in the speed in which the sensor strip is inserted into the measurement device as previously discussed.

Figure 5:
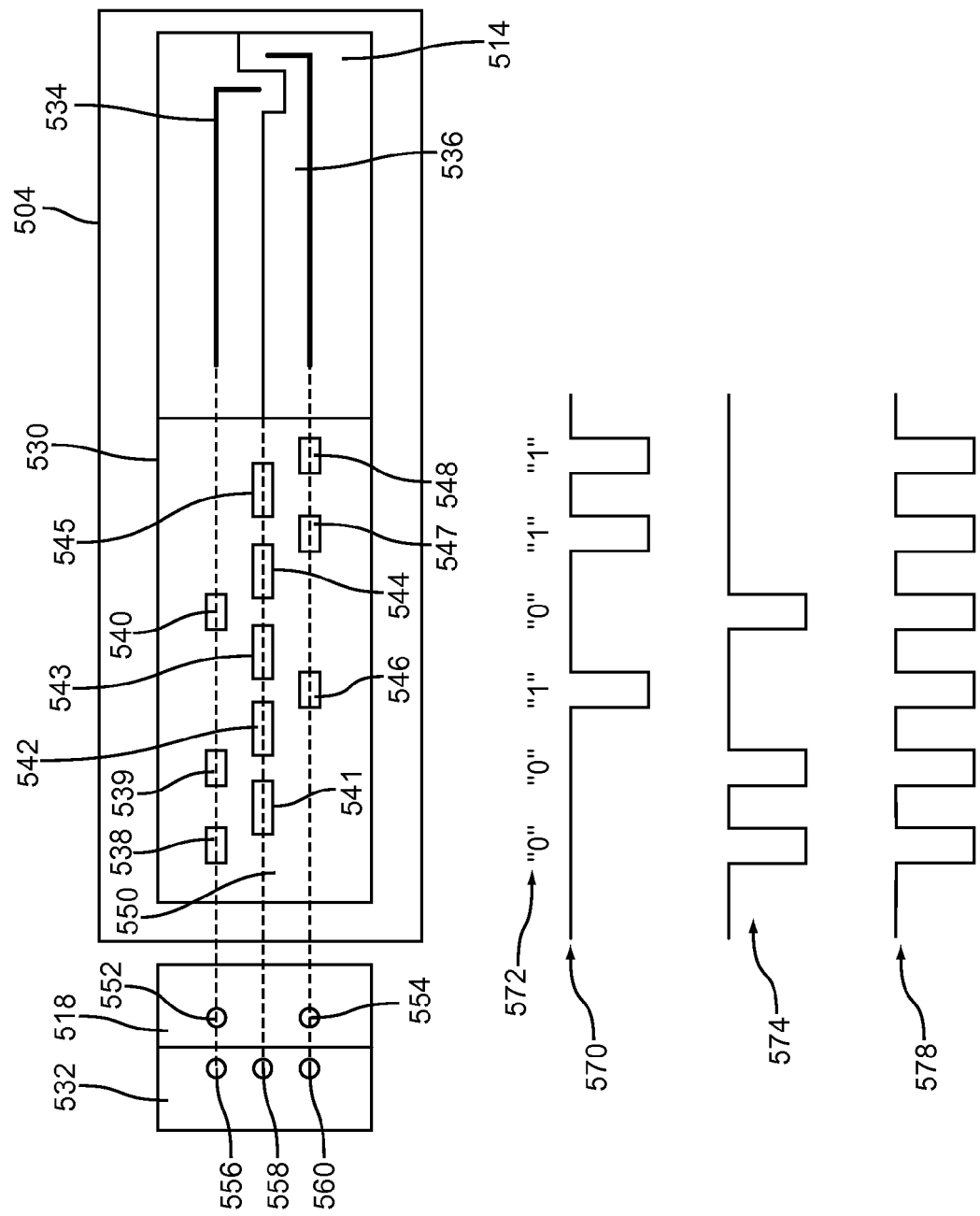
FIG. 5 depicts an additional sensor strip adjacent to a sensor interface and a pattern read device along with code and check signals generated from the sensor strip.

FIG. 5 depicts an additional sensor strip 504 adjacent to a sensor interface 518 and a pattern read device 532 along with code and check signals generated by the sensor strip 504. Sensor strip 504 is similar in configuration and operation to the sensor strip 204 described in relation to FIG. 2. Except in sensor strip 504, the non-conductive areas are formed by removing unwanted portions of a conductive layer on a non-conductive layer to expose non-conductive areas surrounded by conductive areas. While a particular configuration is shown, sensor strip 504, sensor interface 518, and pattern read device 532 may have other configurations including those with additional components. Other code signals may be generated.

The sensor strip 504 includes a sample interface 514 and a sequential conductive pattern 530. The reservoir, channel, and opening of the sensor strip have been omitted for clarity. The sample interface 514 includes a working electrode 534 and a counter electrode 536. The sequential conductive pattern 530 has non-conductive areas 538-548 surrounded by conductive areas 550. The non-conductive areas 538-548 are rectangles of non-conductive material exposed by the removal of the conductive material that forms the conductive areas 550. The non-conductive areas 538-548 may be formed by removing essentially all the conductive material to expose substantially all the non-conductive material within each rectangle. The non conductive areas 538-548 may be formed by removing the conductive material to expose non-conductive material along the perimeter of the rectangle, thus forming an inner conductive portion essentially surrounded by an outer non-conductive portion. The non-conductive areas 538-548 may have other configurations including those with different positions, shapes, and orientations.

The sensor interface 518 includes a first analysis contact 552 and a second analysis contact 554. When the sensor strip 504 is inserted properly into a measurement device, the first analysis contact 552 and second analysis contact 554 connect with the working electrode 534 and the counter electrode, respectively, in the sample interface 514. A processor in the measurement device applies an excitation signal to the working and counter electrodes 534 and 536 through the first and second analysis contacts 552 and 554. The processor does not attempt to apply the excitation signal until the working and counter electrodes 534 and 536 pass the sequential conductive pattern 530.

The pattern read device 532 includes a first test contact 556, a second test contact 558, and a third test contact 560. When the sensor strip is inserted into the measurement device, the processor in the measurement device drives test contact 558 to ground and applies test signals to test contacts 556 and 558. As the sensor strip 504 passes across the pattern read device 532, the test contacts 556, 558, and 560 selectively and sequentially connect with non-conductive areas 538-548 and conductive areas 550 in the sequential conductive pattern 530.

When the test contact 556 connects with the non-conductive areas 538-540, the test contacts 558 and 560 connect with the conductive areas 550 in the sequential conductive pattern 530. When the test contact 558 connects with the non-conductive areas 541-545, the test contacts 556 and 560 are electrically isolated from the test contact 558 at essentially the same time. When the test contact 560 connects with the non-conductive areas 546-548, the tests contacts 556 and 558 connect with the conductive areas 550 in the sequential conductive pattern 530. The non-conductive areas 538-548 may have an area selected to reduce or eliminate the affect a misalignment of the test contacts and/or sensor strip may have. One or more of the non-conductive areas 538-548 may be omitted to connect the second test contact 558 with both the first test contact 556 and the third test contact 560.

FIG. 5 also depicts code signals generated by the sensor strip 504. The first code signal 570 illustrates the sequential connections of the first test contact 556 with non-conductive areas 538-545 and the conductive areas 550 in the sequential conductive pattern 530. The second code signal 574 illustrates the sequential connections of the third test contact 560 with non-conductive areas 541-548 and the conductive areas 550 in the sequential conductive pattern 530. The first code signal 570 and second code signal 574 may be represented by the a logic sequence 572, in which a logic value (0 or 1) indicates the relative output of the code signals at positions on the sensor strip 504. For example, the logic value "0" indicates the first code signal 570 is not grounded and the second code signal 574 is grounded. The logic value "1" indicates the first code signal 570 is grounded and the second code signal 574 is not grounded. Other code signals, logic values, and logic sequences may be used. The first and second code signals 570 and 574 and/or logic sequence 572 may be used to provide coding information to a measurement device in a biosensor system and to detect fault conditions that affect or change the coding information as previously discussed.

Different coding information may be generated by changing the location of the non-conductive areas in the sequential conductive pattern 530. For example, when one or more of the non-conductive areas 538-540 are moved to connect with the third test contact 560; the first test contact 558 then would be connected with the second test contact 558. Thus, the first and second code signals 570 and 574 would change. In the first code signal 570, one or more of the previously non-ground outputs would change to a ground output in response to the move of non-conductive areas 538-540. In the second code signal 574, one or more of the previously ground outputs would change to a non-ground output in response to the move of non-conductive areas 538-540.

Similarly, when one or more of the non-conductive areas 546-548 are moved to connect with the first test contact 556; the third test contact 560 then would be connected with the second test contact 558. Thus, the first and second code signals 570 and 574 would change. In the first code signal 570, one or more of the previously ground outputs would change to a non-ground output in response to the move of non-conductive areas 546-548. In the second code signal 574, one or more of the previously non-ground outputs would change to a ground output in response to the move of non-conductive areas 546-548. Other changes to the connections between the tests contacts and the conductive and non-conductive areas may be made.

FIG. 5 further depicts a check signal 578 generated by the sensor strip 504. The check signal 578 may be represented by a logic sequence. The measurement device combines the first and second code signals 570 and 574 to produce the check signal 578. Other check signals may be used. The measurement device may use the check signal 578 to detect fault conditions in the first and second code signals as previously discussed. The check signal 578 also makes the code signals less sensitive or insensitive to the speed or changes in the speed in which the sensor strip is inserted into the measurement device as previously discussed.

Figure 6:
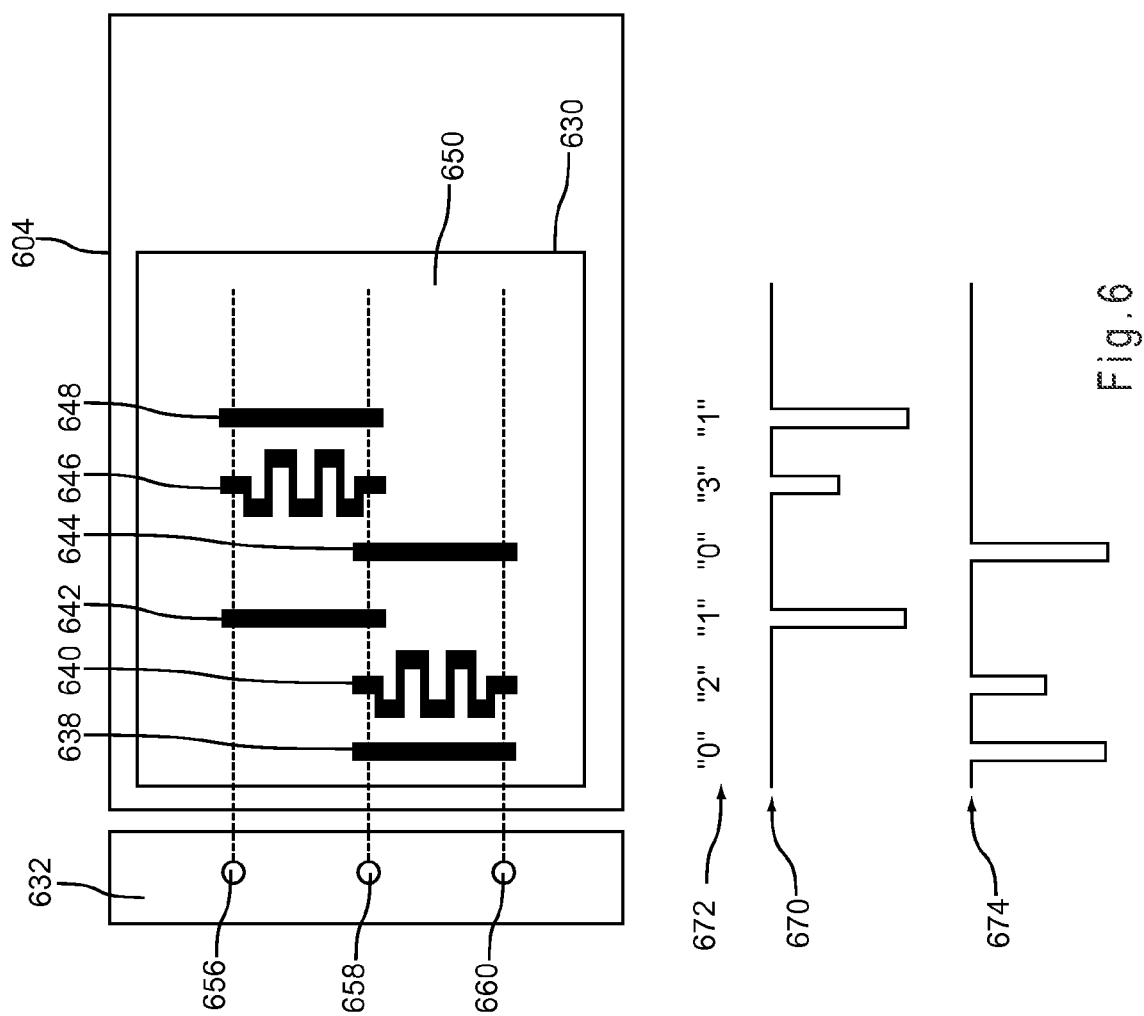
FIG. 6 depicts a further sensor strip adjacent to a sensor interface and a pattern read device along with code signals generated from the sensor strip.

FIG. 6 depicts a further sensor strip 604 adjacent to a pattern read device 632 along with code signals generated by the sensor strip 604. The sensor interface has been omitted for clarity. While a particular configuration is shown, the sensor strip 604 and the pattern read device 632 may have other configurations including those with additional components. Other code signals may be generated.

The sensor strip 604 includes a sequential conductive pattern 630. The sample interface, reservoir, channel, and opening of the sensor strip have been omitted for clarity. The sequential conductive pattern 630 has conductive areas 638, 640, 642, 644, 646, and 648 disposed on a non-conductive layer, which forms non-conductive areas 650. The conductive areas 638, 640, 642, 644, 646, and 648 are traces of conductive material disposed sequentially in positions substantially perpendicular to the direction the sensor strip 604 moves when inserted into a measurement device. The conductive areas 638, 640, 642, 644, 646, and 648 may have other configurations including those where one or more of the conductive areas connects all the test contacts. The conductive areas 638, 640, 642, 644, 646, and 648 may be disposed in different positions and orientations.

The electrical resistance of the conductive material in each conductive area 638, 640, 642, 644, 646, and 648 may be selected to alter the amount of a test signal transmitted through the particular conductive area. The conductive areas 640 and 646 each have a higher resistance than conductive areas 638, 642, 644 and 648. Thus, the conductive areas 640 and 646 each transmit less of a test signal than the conductive areas 638, 642, 644 and 648. By transmitting less of a test signal, the conductive areas 640 and 646 may partially ground the non-ground test contacts. The conductive areas 638, 640, 642, 644, 646, and 648 may have other resistances.

The amount of the test signal transmitted through each conductive area may be used to provide more coding information than determining only whether the conductive areas are transmitting or not transmitting the test signals. The amount of test signal transmitted through a conductive area is inversely proportional to the resistance in the conductive area and may be measured by a measurement device. By changing the resistance of the conductive areas, the different amounts of each test signal transmitted through the conductive areas may provide additional coding information.

The resistance of the conductive areas may be changed by increasing or decreasing the length of the connection between the test contacts. A higher resistance would result from a longer connection, while a lower resistance would result from a shorter connection. The resistance of the conductive areas also may be changed by varying the conductive material thickness or selecting conductive materials with different bulk resistivity.

The resistance, R, of a rectangular block of material may be calculated by the following equation:

$$R = \frac{\rho L}{A} = \frac{\rho L}{tW}. \quad \text{(Equation 1)}$$

Where $\rho$ is the material bulk resistivity, L is the length, A is the cross sectional area, W is the width, and t is the material thickness.

The pattern read device 632 includes a first test contact 656, a second test contact 658, and a third test contact 660. When the sensor strip is inserted into the measurement device, the processor in the measurement device drives test contact 658 to ground and applies test signals to test contacts 656 and 658. As the sensor strip 604 passes across the pattern read device 632, the test contacts 656, 658, and 660 selectively and sequentially connect with conductive areas 638, 640, 642, 644, 646, and 648 and non-conductive areas 650 in the sequential conductive pattern 630.

When the first and second test contacts 656 and 658 connect with the conductive areas 642, 646, and 648, the third test contact 660 connects with the non-conductive areas in the sequential conductive pattern 630. Since the conductive area 646 has a higher resistance than the conductive areas 642 and 648, the conductive area 646 transmits less of the test signal between test contacts 656 and 658 than the conductive areas 642 and 648. Thus, the first test contact 656 may be partially grounded by the connection with the second test contact 658 through the conductive area 646. In contrast, the first test contact 656 may be grounded by the connection with the second test contact 658 through the conductive areas 642 and 648. The differences between the amount of test signal transmitted through each conductive area 642, 646, and 648 may provide additional coding information.

When the second and third test contacts 658 and 660 connect with conductive areas 638, 640, and 644, the first test contact 656 connects with the non-conductive areas in the sequential conductive pattern 630. Since the conductive area 640 has a higher resistance than the conductive areas 638 and 644, the conductive area 640 will transmit less of the test signal between test contacts 658 and 660 than the conductive areas 638 and 644. Thus, third first test contact 660 may be partially grounded by the connection with the second test contact 658 through the conductive area 640. In contrast, the third test contact 660 may be grounded by the connection with the second test contact 658 through the conductive areas 632 and 644. The differences between the amount of test signal transmitted through each conductive area 642, 646, and 648 may provide additional coding information.

FIG. 6 also depicts the first and second code signals 670 and 674 generated by the sensor strip 604. The first code signal 670 illustrates the sequential connections of the first test contact 656 with non-conductive areas 650 and the conductive areas 642, 646, and, 648 in the sequential conductive pattern 630. The second code signal 674 illustrates the sequential connections of the third test contact 660 with non-conductive areas 650 and the conductive areas 638, 640, and, 644 in the sequential conductive pattern 630. Other code signals may be used.

FIG. 6 also depicts a logic sequence 672 for the code signals. In the logic sequence 672, a logic value (0, 1, 2, or 3) indicates the relative output of the code signals at positions on the sensor strip 604. For example, the logic value "0" indicates the first code signal 670 is not grounded and the second code signal 674 is grounded through a lower resistance connection, such as when the third test contact 660 and the second test contact 658 connect with conductive areas 638 and 644. The logic value "1" indicates the second code signal 674 is not grounded and the first code signal 670 is grounded through a lower resistance connection, such as when the first test contact 656 and the second contact 658 connect with conductive areas 642 and 648. The logic value "2" indicates the first code signal 670 is not grounded and the second code signal 674 is partially grounded through a higher resistance connection, such as when the third test contact 660 and the second test contact 658 connect with conductive area 640. The logic value "3" indicates the second code signal 674 is not grounded and the first code signal 670 is grounded through a higher resistance connection, such as when the first test contact 656 and the second contact 658 connect with conductive area 646. Thus, the presence of the conductive areas represents four different logic values, or base 4 coding. Additional resistance values may be used to represent more logic values. Other logic values and logic sequences may be used.

The first and second code signals 670 and 674 and/or logic sequence 672 may be used, as previously discussed, to provide coding information to a measurement device in a biosensor system and to detect fault conditions that affect or change the coding information. Different coding information may be generated by changing the location of the conductive areas in the sequential conductive pattern 630. The first and second code signals 670 and 674 may be combined to generate a check signal as previously discussed.

Figure 7:
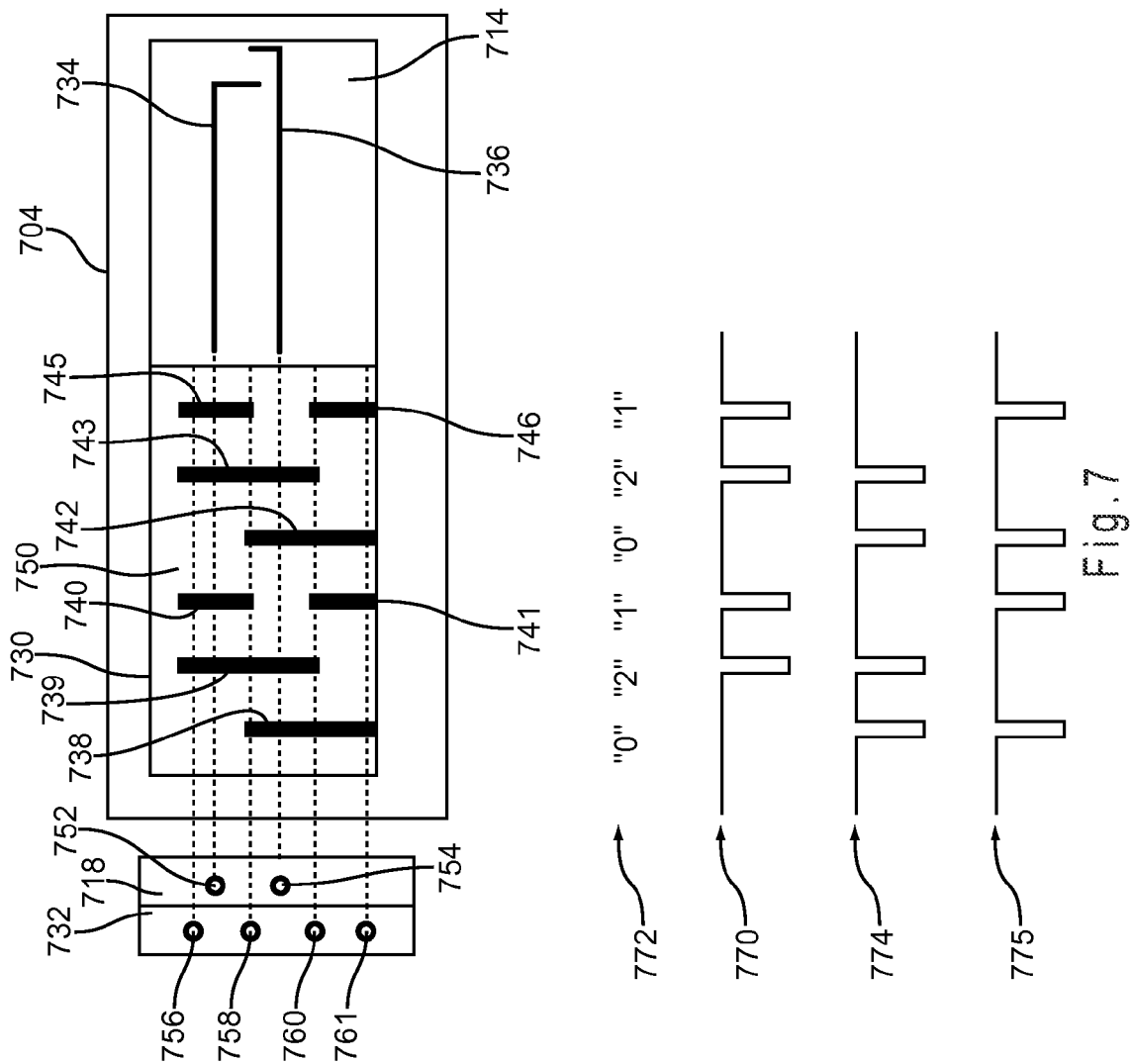
FIG. 7 depicts another sensor strip adjacent to a sensor interface and a pattern read device along with code signals generated from the sensor strip.

FIG. 7 depicts another sensor strip 704 adjacent to a sensor interface 718 and a pattern read device 732 along with code signals generated by the sensor strip 704. While a particular configuration is shown, the sensor strip 704, the sensor interface 718, and the pattern read device 732 may have other configurations including those with additional components. Other code signals may be generated.

The sensor strip 704 includes a sample interface 714 and a sequential conductive pattern 730. The reservoir, channel, and opening of the sensor strip have been omitted for clarity. The sample interface 714 includes a working electrode 734 and a counter electrode 736. The sequential conductive pattern 730 has conductive areas 738-746 disposed on a non-conductive layer, which forms non-conductive areas 750. The conductive areas 738-746 are traces or thin rectangles of conductive material disposed sequentially in positions essentially equidistant from each other and substantially perpendicular to the direction the sensor strip 704 moves when inserted into a measurement device. The conductive areas 738-746 may have other configurations and may be disposed in different positions and orientations.

The sensor interface 718 includes a first analysis contact 752 and a second analysis contact 754. When the sensor strip 704 is inserted properly into a measurement device, the first analysis contact 752 and second analysis contact 754 connect with the working electrode 734 and the counter electrode, respectively, in the sample interface 718. A processor in the measurement device applies an excitation signal to the working and counter electrodes 734 and 736 through the first and second analysis contacts 752 and 754. The processor does not attempt to apply the excitation signal until the working and counter electrodes 734 and 736 pass the sequential conductive pattern 730.

The pattern read device 732 includes a first test contact 756, a second test contact 758, a third test contact 760, and a fourth test contact 761. When the sensor strip 704 is inserted into the measurement device, the sequential conductive pattern 730 passes across the pattern read device 732. The test contacts 756, 758, 760, and 761 selectively and sequentially connect with conductive areas 738-746 and non-conductive areas 750 in the sequential conductive pattern 730.

The lengths and positions of the conductive areas 738-746 may be selected to connect with two pairs of adjacent test contacts at each position on the sequential conductive pattern 730, while the third pair of adjacent test contacts is connected with non-conductive areas 750. The pairs of adjacent test contacts are the first and second test contacts 756 and 758, the second and third test contacts 758 and 760, and the third and fourth test contacts 760 and 761.

FIG. 7 also depicts code signals generated by the sensor strip 704. The first code signal 770 illustrates the sequential connections of the first and second test contacts 756 and 758 with non-conductive areas 750 and the conductive areas 739, 740, 743, and 745 in the sequential conductive pattern 730. The second code signal 774 illustrates the sequential connections of the second and third test contacts 758 and 760 with non-conductive areas 750 and the conductive areas 738, 739, 742, and 743 in the sequential conductive pattern 730. The third code signal 775 illustrates the sequential connections of the third and fourth test contacts 760 and 761 with non-conductive areas 750 and the conductive areas 738, 740, 741, and 746 in the sequential conductive pattern 730. Other code signals may be used.

The code signals 770, 774, and 775 may be represented by the logic sequence 772, which is ternary (base 3) encoding. With ternary coding, each position on the sequential conductive pattern 730 encodes three levels. The sequential conductive pattern 730 illustrates six positions, which provides 729 distinct values that may be encoded on sensor strip 704. In logic sequence 772, a logic value (0, 1, or 2) indicates the relative output of the code signals at positions on the sensor strip 704. For example, the logic value "0" indicates the first code signal 770 is not grounded and the second and third code signals 774 and 775 are grounded. The logic value "1" indicates the first and third code signals 770 and 775 are grounded and the second code signal 774 is not grounded. The logic value "2" indicates the first and second code signals 770 and 774 are grounded and the third code signal 775 is not grounded. Other logic values and logic sequences may be used.

Table 2 lists the number of different code sequences with ternary coding (base 3) in relation to the number of conductive areas in a sequential read pattern. Other numbers of conductive areas may be used.

TABLE 2

| Number of Conductive Areas | Number of Different Code Sequences |
|---|---|
| 1 | 3 |
| 2 | 9 |
| 3 | 27 |
| 4 | 81 |
| 5 | 243 |
| 6 | 729 |
| 7 | 2187 |
| 8 | 6561 |
| 9 | 19683 |
| 10 | 59049 |

Additional test contacts may be used to increase the available codes at each position. With five test contacts, each position multiplies the number of levels by four. With six test contacts, each position multiplies the number of levels by five. Other numbers of contacts may be used.

The code signals and/or logic sequence may be used to provide coding information to a measurement device in a biosensor system. The code signals may be combined to generate a check signal. Different coding information may be generated by changing the location of the conductive areas in the sequential conductive pattern.

The code signals may be used to detect fault conditions. At each position of conductive areas on a sequential conductive pattern, two pairs of adjacent test contacts are connected with one or more conductive areas, and the third pair of adjacent test contacts is connected with the non-conductive area. If there is a fault condition where a connection with the conductive areas is not made, then there will be too few positions detected by the measurement device. If there is a fault condition where a connection is made that should not be made, then there will be too many positions detected by the measurement device.

Figure 8:
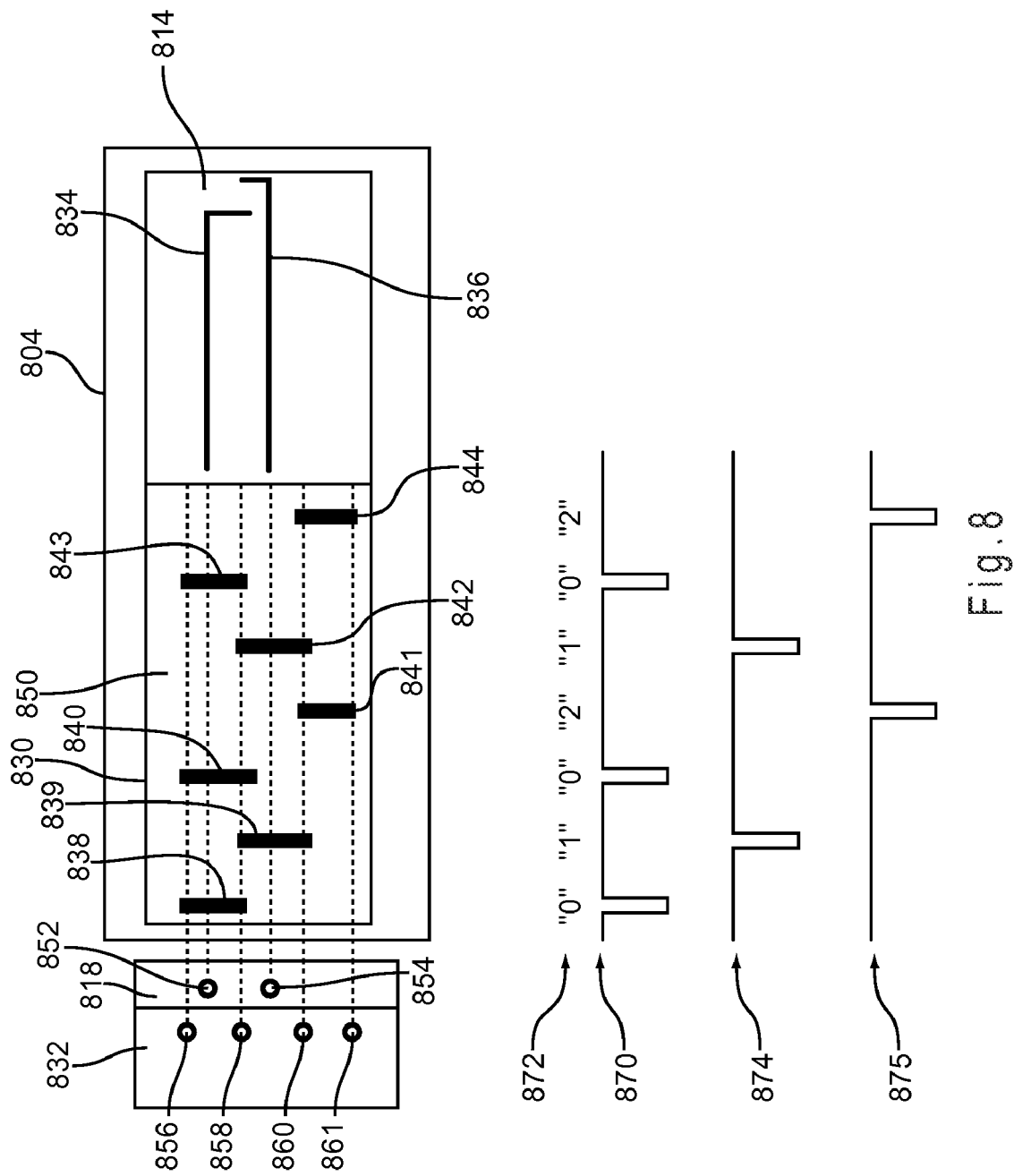
FIG. 8 depicts another sensor strip adjacent to a sensor interface and a pattern read device along with code signals generated from the sensor strip.

FIG. 8 depicts another sensor strip 804 adjacent to a sensor interface 818 and a pattern read device 838 along with code signals generated by the sensor strip 804. While a particular configuration is shown, the sensor strip 804, the sensor interface 818, and the pattern read device 832 may have other configurations including those with additional components. Other code signals may be generated.

The sensor strip 804 includes a sample interface 814 and a sequential conductive pattern 830. The reservoir, channel, and opening of the sensor strip have been omitted for clarity. The sample interface 814 includes a working electrode 834 and a counter electrode 836. The sequential conductive pattern 830 has conductive areas 838-844 disposed on a non-conductive layer, which forms non-conductive areas 850. The conductive areas 838-844 are traces or thin rectangles of conductive material disposed sequentially in positions essentially equidistant from each other and substantially perpendicular to the direction the sensor strip 804 moves when inserted into a measurement device. The conductive areas 838-844 may have other configurations and may be disposed in different positions and orientations.

The sensor interface 818 includes a first analysis contact 852 and a second analysis contact 854. When the sensor strip 804 is inserted properly into a measurement device, the first analysis contact 852 and second analysis contact 854 connect with the working electrode 834 and the counter electrode, respectively, in the sample interface 814. A processor in the measurement device applies an excitation signal to the working and counter electrodes 834 and 836 through the first and second analysis contacts 852 and 854. The processor does not attempt to apply the excitation signal until the working and counter electrodes 834 and 836 pass the sequential conductive pattern 830.

The pattern read device 832 includes a first test contact 856, a second test contact 858, a third test contact 860, and a fourth test contact 861. When the sensor strip 804 is inserted into the measurement device, the sequential conductive pattern 830 passes across the pattern read device 832. The test contacts 856, 858, 860, and 861 selectively and sequentially connect with conductive areas 838-844 and non-conductive areas 850 in the sequential conductive pattern 830.

The lengths and positions of the conductive areas 838-844 may be selected to connect with one pair of adjacent test contacts at each position on the sequential conductive pattern 830, while the other two pairs of adjacent test contacts are connected with non-conductive areas 850. The pairs of adjacent test contacts are the first and second test contacts 856 and 858, the second and third test contacts 858 and 860, and the third and fourth test contacts 860 and 861.

FIG. 8 also depicts code signals generated by the sensor strip 804. The first code signal 870 illustrates the sequential connections of the first and second test contacts 856 and 858 with non-conductive areas 850 and the conductive areas 838, 840, and 843 in the sequential conductive pattern 830. The second code signal 874 illustrates the sequential connections of the second and third test contacts 858 and 860 with non-conductive areas 850 and the conductive areas 839 and 842 in the sequential conductive pattern 830. The third code signal 875 illustrates the sequential connections of the third and fourth test contacts 860 and 861 with non-conductive areas 850 and the conductive areas 841, 842, and 844 in the sequential conductive pattern 830. The code signals may be represented by a logic sequence. Other code signals may be used.

The code signals 870, 874, and 875 may be represented by the logic sequence 872, which also is ternary (base 3) encoding as previously discussed. In logic sequence 872, a logic value (0, 1, or 2) indicates the relative output of the code signals at positions on the sensor strip 804. For example, the logic value "0" indicates the first code signal 870 is grounded and the second and third code signals 874 and 875 are not grounded. The logic value "1" indicates the first and third code signals 870 and 875 are not grounded and the second code signal 874 is grounded. The logic value "2" indicates the first and second code signals 870 and 874 are not grounded and the third code signal 875 is grounded. Other logic values and logic sequences may be used.

The code signals and/or logic sequence may be used to provide coding information to a measurement device in a biosensor system and to detect fault conditions. The code signals may be combined to generate a check signal. Different coding information may be generated by changing the location of the conductive areas in the sequential conductive pattern.

FIG. 9 depicts another electrical detection circuitry 962 in a pattern read device. The electrical detection circuitry 962 includes a first buffer circuit 964 connected to the first test contact 956, a ground 966 connected to the second test contact 958, and a second buffer circuit 968 connected to the third test contact 960. The electrical detection circuitry 962 enables the first and third test contacts 956 and 960 to be used as analysis contacts due to switches in the buffer circuits 964 and 968 that connect the test contacts with the processor and/or signal generator in the measurement device. Other electrical detection circuitry may be used.

The first buffer circuit 964 includes input potential $V_{cc}$ connected through resister R1 to switch SW1 and the input of a buffer U1. Switch SW1 is connected to the first test contact 956 and to a first input conductor 980 from a processor and/or signal generator in the measurement device. The output of buffer U1 is connected to a processor in the measurement device via a first output conductor 982.

In use, switch SW1 initially connects the first test contact 956 with the input of buffer U1 while the sequential conductive pattern on a sensor strip passes across the pattern read device. When the first test contact 956 connects with the second test contact 958 through a conductive area on the sequential conductive pattern 930, the input of buffer U1 becomes ground and the corresponding output of buffer U1 is at logic zero ("0"). When the first test contact 956 connects with a non-conductive area on the sequential conductive pattern 930, the input of buffer U1 is pulled high by the input resistor R1 and the corresponding output of buffer U1 is at logic one ("1"). The sequential output of the buffer U1 generates a code signal.

After the first test contact 956 moves past the pattern read device and connects with the working or other electrode on the sensor strip, the switch SW1 connects the first test contact 956 with the first input conductor 980. The switch SW1 disconnects the first test contact 956 from the input of buffer U1. The processor and/or signal generator in the measurement device applies the excitation signal to the working or other electrode through the first input conductor 980, switch SW1, and the first test contact 956. The switch SW1 may be controlled by the processor using software stored in the storage medium.

The second buffer circuit 968 includes input potential $V_{cc}$ connected through resister R2 to switch SW2 and the input of a buffer U2. Switch SW2 is connected to the third test contact 960 and to a second input conductor 984 from a processor and/or signal generator in the measurement device. The output of buffer U2 is connected to a processor in the measurement device via a second output conductor 986.

In use, switch SW2 initially connects the third test contact 960 with the input of buffer U2 while the sequential conductive pattern on a sensor strip passes across the pattern read device. When the third test contact 960 connects with the second test contact 958 through a conductive area on the sequential conductive pattern 930, the input of buffer U2 becomes ground and the corresponding output of buffer U2 is at logic zero ("0"). When the third test contact 960 connects with a non-conductive area on the sequential conductive pattern 930, the input of buffer U2 is pulled high by the input resistor R1 and the corresponding output of buffer U2 is at logic one ("1"). The sequential output of the buffer U2 generates a code signal.

After the third test contact 960 moves past the pattern read device and connects with the counter or other electrode on the sensor strip, the switch SW1 connects the third test contact 960 with the second input conductor 984. The switch SW2 disconnects the third test contact 960 from the input of buffer U2. The processor and/or signal generator in the measurement device applies the excitation signal to the counter or other electrode through the second input conductor 984, switch SW2, and the third test contact 960. The switch SW2 may be controlled by the processor using software stored in the storage medium.

Figure 10:
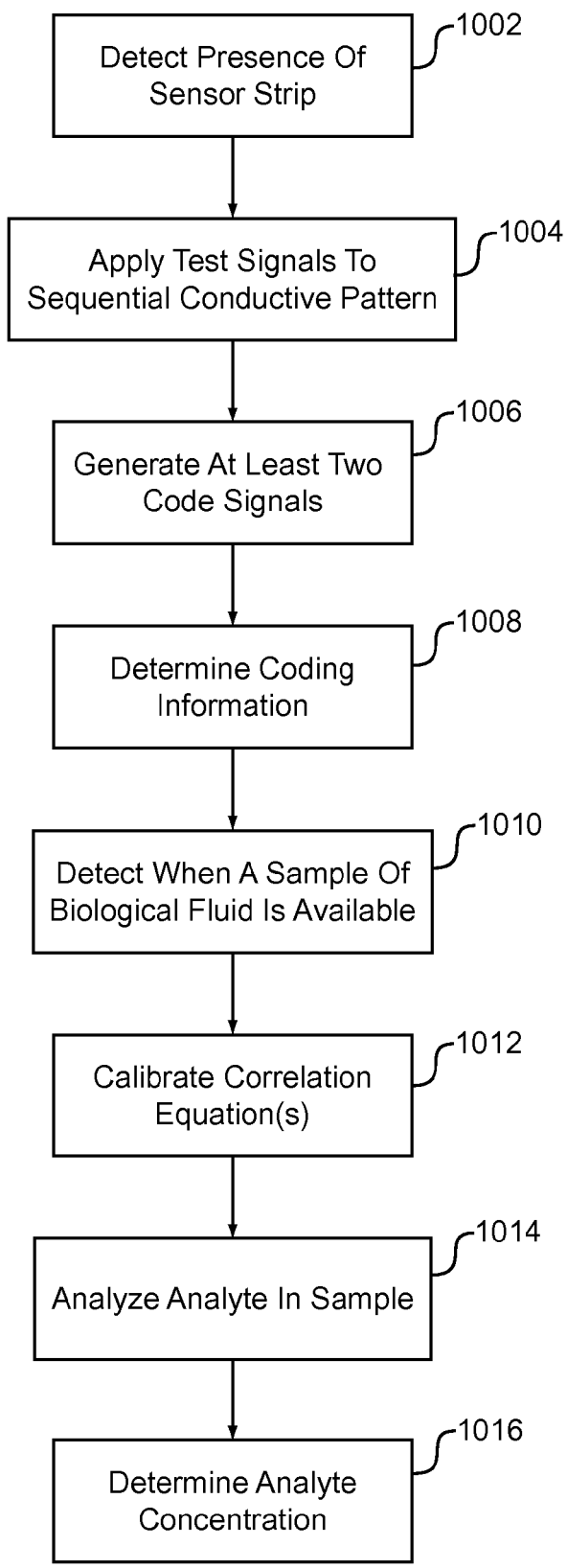
FIG. 10 represents a method for calibrating an analysis of an analyte in a biological fluid.

FIG. 10 represents a method for calibrating an analysis of an analyte in a biological fluid. In 1002, a measurement device detects the presence of a sensor strip in a biosensor. In 1004, the measurement device applies test signals to a sequential conductive pattern. In 1006, the sequential conductive pattern generates at least two code signals. In 1008, the measurement device determines coding information in response to code signals. In 1010, the measurement device detects when a sample of a biological fluid is available for analysis. In 1012, the measurement device calibrates one or more correlation equations in response to the coding information. In 1014, the measurement device analyzes the analyte in the sample. In 1016, the measurement device determines the analyte concentration of the biological fluid using one or more calibrated correlation equations.

In 1002, the measurement device detects when a sensor strip is present. The measurement device may sense when a sensor strip is placed in the biosensor. The measurement device may sense (mechanically, electrically, or the like) when electrical contacts in the measurement device connect with electrical conductors and/or the sequential conductive pattern on the sensor strip. The measurement device may apply a one or more signals to the conductors and/or electrodes to detect when a sensor strip is present. The measurement device may apply a one or more signals to the sequential conductive pattern to detect when a sensor strip is present. The measurement device may use other methods and devices to detect when a sensor strip is present in a biosensor including user input.

In 1004, the measurement device applies test signals to the sequential conductive pattern. The measurement device selectively and sequentially connects test contacts with intermittent conductive and non-conductive areas on the sequential conductive pattern as previously discussed. The measurement device drives one test contact to ground and applies the test signals to the other test contacts as previously discussed.

In 1006, the sequential conductive pattern generates code signals in response to the test signals. The test contacts selectively and sequentially connect with the conductive and non-conductive areas at different positions. At each position, the conductive areas connect one or more non-ground test contacts with the test contact driven to ground. The non-conductive areas essentially prevent electrical communication between the test contacts. At different positions on the sequential read pattern, the conductive and non-conductive areas may connect with the same or different non-ground test contacts. When the connections with the conductive and non-conductive areas are the same, the test contacts have the same ground and non-ground test signals. When the connections with the conductive and non-conductive areas are different, the test contacts have different ground and non-ground test signals. This selective and sequential switching or non-switching between ground and non-ground test signals generates one or more code signals as previously discussed.

In 1008, the measurement device determines the coding information in response to the code signals. The coding information may be any information used to adjust correlation equations for electrochemical and/or optical analyses, identify the sensor strip, and the like as previously discussed. The measurement device may select stored reference parameters and adjustments in response the coding information or code signals.

In 1010, the measurement device detects when a sample of biological fluid is available for analysis. The measurement device may sense (mechanically, electrically, or the like) when electrical conductors in the sensor strip are in contact with a sample. The measurement device may apply one or more signals to the working, counter, and/or other electrodes to detect when a sample connects with the electrodes. The biosensor may use other methods and devices to detect when a sample is available for analysis.

In 1012, the measurement device calibrates one or more correlation equations in response to the coding information. Correlation equations may be used to determine the analyte concentration in optical and/or electrochemical analyzes as previously discussed.

In 1014, the measurement device analyzes the analyte in the sample using an electrochemical analysis, an optical analysis, a combination thereof, or the like. In an electrochemical analysis, the measurement device may use one or more electrochemical processes as previously discussed. The measurement device measures and correlates an output signal from a redox reaction of the analyte with the analyte concentration. In an optical analysis, the measurement device measures the amount of light absorbed or generated by the reaction of a chemical indicator with the analyte as previously discussed. The measurement device measures and correlates the amount of light with the analyte concentration.

In 1016, the measurement device determines the analyte concentration in the sample of the biological fluid. The measurement device may use one or more of the calibrated correlation equations to determine the analyte concentration of the sample. The measurement device may use the calibrated analyte value or other result to determine the analyte concentration of the sample.

While various embodiments of the invention have been described, it will be apparent to those of ordinary skill in the art that other embodiments and implementations are possible within the scope of the invention.

What is claimed is:

1. A biosensor for determining an analyte concentration in a biological fluid, comprising:
   a measurement device having a processor connected to a pattern read device;
   a sensor strip having a sequential conductive pattern, the sequential conductive pattern including conductive and non-conductive areas;

where the measurement device and sensor strip implement an analyte analysis, where the analyte analysis has at least one correlation equation;

where the pattern read device applies test signals to the sequential conductive pattern and includes test contacts, the pattern read device selectively and sequentially connecting the test contacts with conductive and non-conductive areas on the sequential conductive pattern;

where the sequential conductive pattern generates at least two code signals in response to the test signals;

where the processor calibrates at least one correlation equation responsive to the code signals; and where the processor determines an analyte concentration responsive to at least one calibrated correlation equation.

2. The biosensor of claim 1, where the pattern read device applies test signals to at least two test contacts, and where the pattern read device drives at least one test contact to ground.

3. The biosensor of claim 1, where the processor generates a check signal in response to the code signals.

4. The biosensor of claim 1, where the pattern read device drives at least one test contact partially to ground.

5. The biosensor of claim 1, where the processor determines coding information in response to the code signals.

6. The biosensor of claim 1, where the analyte analysis is an electrochemical analysis.

7. The biosensor of claim 1, where the processor checks for errors in the code signals.

8. The biosensor of claim 7, where the processor enforces at least one rule regarding simultaneously electrically connected signals.

9. A biosensor for determining an analyte concentration in a biological fluid, comprising:
a measurement device having a processor connected to a pattern read device, where the pattern read device has at least three test contacts;
a sensor strip having a sequential conductive pattern, where the sequential conductive pattern has at least one conductive area and at least one non-conductive area;
where the pattern read device applies test signals to at least two test contacts;
where the pattern read device drives at least one test contact to ground;
where the pattern read device selectively and sequentially connects the test contacts with the conductive and non-conductive areas on the sequential conductive pattern;
where the sequential conductive pattern generates at least two code signals in response to the test signals;
where the measurement device and sensor strip implement an analyte analysis, where the analyte analysis has at least one correlation equation;
where the processor calibrates at least one correlation equation responsive to the code signals; and
where the processor determines an analyte concentration responsive to at least one calibrated correlation equation.

10. The biosensor of claim 9, comprising at least one conductive area with a higher resistance than another conductive area.

11. The biosensor of claim 9, where the processor generates a check signal in response to the code signals.

12. The biosensor of claim 9, where the pattern read device drives at least one test contact partially to ground.

13. The biosensor of claim 9, where the processor determines coding information in response to the code signals.

14. The biosensor of claim 9, further comprising electrical detection circuitry.

15. The biosensor of claim 9, where the processor checks for errors in the code signals.

16. The biosensor of claim 15, where the processor enforces at least one rule regarding simultaneously electrically connected signals.

17. A method for calibrating an analysis of an analyte in a biological fluid, comprising:
applying test signals to a sequential conductive pattern, the sequential conductive pattern including conductive and non-conductive areas;
selectively and sequentially connecting test contacts with conductive and non-conductive areas on the sequential conductive pattern;
generating at least two code signals in response to the test signals;
calibrating at least one correlation equation in response to the code signals; and determining an analyte concentration in response to at least one calibrated correlation equation;
where the analyte concentration is determined by
reacting the analyte through a chemical reaction selected from the group consisting of a reaction with a chemical indicator and a redox reaction, where the chemical reaction produces an output signal,
measuring the output signal, and
calculating the analyte concentration using the at least one calibrated correlation equation and the measured output signal.

18. The method of claim 17, further comprising applying test signals to at least two test contacts on the sequential conductive pattern, and driving at least one test contact to ground.

19. The method of claim 17, further comprising generating a check signal in response to the code signals.

20. The method of claim 17, further comprising driving at least one test contact partially to ground.

21. The method of claim 17, further comprising determining coding information in response to the code signals.

22. The method of claim 17, further comprising checking for errors in the code signals.

23. The method of claim 22, further comprising enforcing at least one rule regarding simultaneously electrically connected signals.

* * * * *